United States Patent [19]

Miller

[11] Patent Number: 4,846,181

[45] Date of Patent: Jul. 11, 1989

[54] SOFT TISSUE WOUND HEALING THERAPY UTILIZING PULSED ELECTRICAL STIMULATION

[75] Inventor: Katherine H. Miller, Centreville, Va.

[73] Assignee: Staodynamics, Inc., Longmont, Colo.

[21] Appl. No.: 103,696

[22] Filed: Oct. 2, 1987

[51] Int. Cl.$^4$ .................... A61N 1/00; H05G 00/00
[52] U.S. Cl. ................................................ 128/421
[58] Field of Search ................ 128/419 R, 421, 422, 128/783, 788, 802, 803

[56] References Cited

U.S. PATENT DOCUMENTS

| | | | |
|---|---|---|---|
| 2,099,511 | 11/1931 | Caesar | 128/421 |
| 3,893,462 | 7/1975 | Manning | 128/421 |
| 3,918,459 | 11/1975 | Horn . | |
| 3,924,641 | 12/1975 | Weiss | 128/421 |
| 3,933,147 | 1/1976 | Du Vall et al. | 128/788 |
| 3,946,745 | 3/1976 | Hsiang-Lai et al. | 128/421 |
| 3,964,477 | 6/1976 | Ellis et al. | 128/421 |
| 4,019,510 | 4/1977 | Ellis | 128/421 |
| 4,105,017 | 8/1978 | Ryaby et al. | 128/421 |
| 4,233,965 | 11/1980 | Fairbanks | 128/421 |
| 4,312,340 | 1/1982 | Donadelli | 128/421 |
| 4,313,438 | 2/1982 | Greatbatch | 128/419 F |
| 4,314,554 | 2/1982 | Greatbatch | 128/419 F |
| 4,541,432 | 9/1985 | Molina-Negro et al. | 128/421 |
| 4,556,051 | 12/1985 | Maurer | 128/421 |
| 4,646,744 | 3/1987 | Capel | 128/423 R |
| 4,754,759 | 7/1988 | Allocca | 128/421 |

OTHER PUBLICATIONS

Alvarez, "The Healing of Superficial Skin Wounds is Stimulated by External Electrical Current", The Journal of Investigative Dermatology, 81:144–148, 1983.
Assimacopoulos, "Low Intensity Negative Electric Current in the Treatment of Ulcers of the Leg due to Chronic Venous Insufficiency", American Journal of Surgery, vol. 115, May 1968, pp. 683–687.
Frank and Szeto, "A Review of Electromagnetically Enhanced Soft Tissue Healing", IEEE Engineering in Medicine and Biology Magazine, Dec., 1983, pp. 27–32.
Gault and Gatens, "Use of Low Intensity Direct Current in Management of Ischemic Skin Ulcers", Physical Therapy, vol. 56/No. 3, Mar. 1976, pp. 265–269.
Wolcott, "Accelerated Healing of Skin Ulcers by Electrotherapy", Southern Medical Journal, vol. 62, Jul. 1969, pp. 795–801.
Ross and Segal, "High Voltage Galvanic Stimulation—An Aid to Post-Operative Healing", Current Podiatry, May 1981, pp. 19–25.
Thurman and Christian, "Response of a Serious Circulatory Lesion to Electrical Stimulation", Physical Therapy, vol. 51/No. 10, Oct. 1971, pp. 1107–1110.
Nickerson, "High Voltage/Low Intensity Current in Wound Healing", Poster Session APTA National Meeting, Phoenix, Jun. 17, 1980.
Young, "Electric Impulse Therapy Aids Wound Healing", Modern Veterinary Practice, Dec. 1966.
Akers and Gabrielson, "The Effect of High Voltage Galvanic Stimulation on the Rate of Healing of Decubitus Ulcers", ISA, 1984, 0-87664-805-7/84, pp. 99–100.

Primary Examiner—Francis Jaworski
Assistant Examiner—George Manuel
Attorney, Agent, or Firm—Robert E. Harris

[57] ABSTRACT

Wound healing therapy utilizing pulsed electrical stimulation is disclosed with the process including repeated short treatments of electrical stimulation applied to a soft tissue wound through an active electrode positioned preferably at the wound and with a dispersive electrode positioned at a distance from the wound. The active electrode positioned at the wound is normally caused to have negative pulses applied therethrough to the wound during a first treatment period of a treatment cycle, and thereafter is made to have positive pulses applied therethrough to the wound during a second treatment period of the treatment cycle, with the treatment cycle being preferably thereafter repeated one or more times in treating most wounds, and with the negative pulses causing debriding of the wound. Effectively treated soft tissue wounds include partial thickness and full thickness open skin wounds, and particularly chronic ulcers, burns, and skin flaps by way of example, with electrical stimulation being effected by both direct pad and hydrotherapy applications utilizing an electrical pulse stimulating unit capable of delivering pulses at a predetermined pulse intensity and rate.

31 Claims, 5 Drawing Sheets

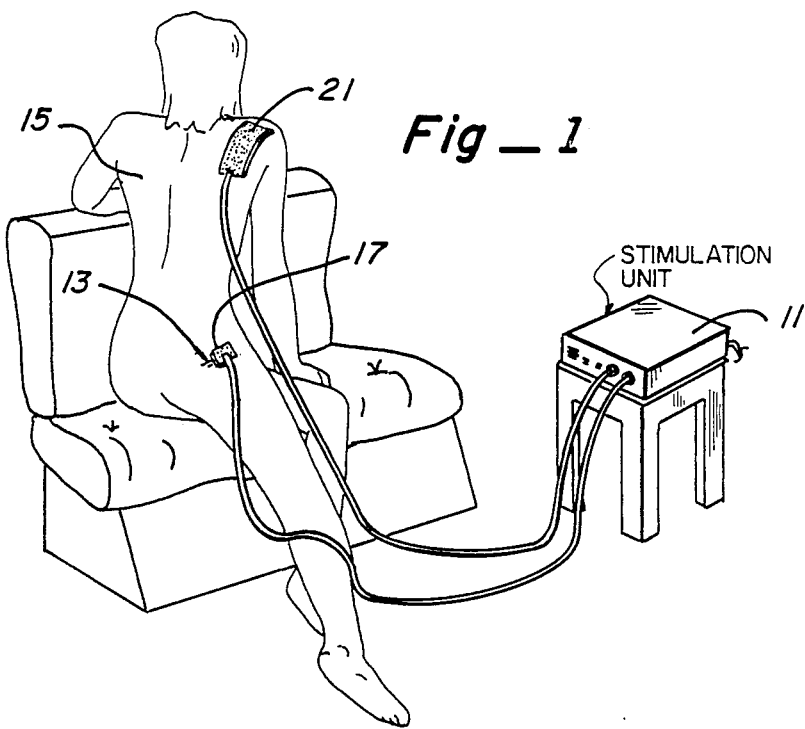
Fig_1
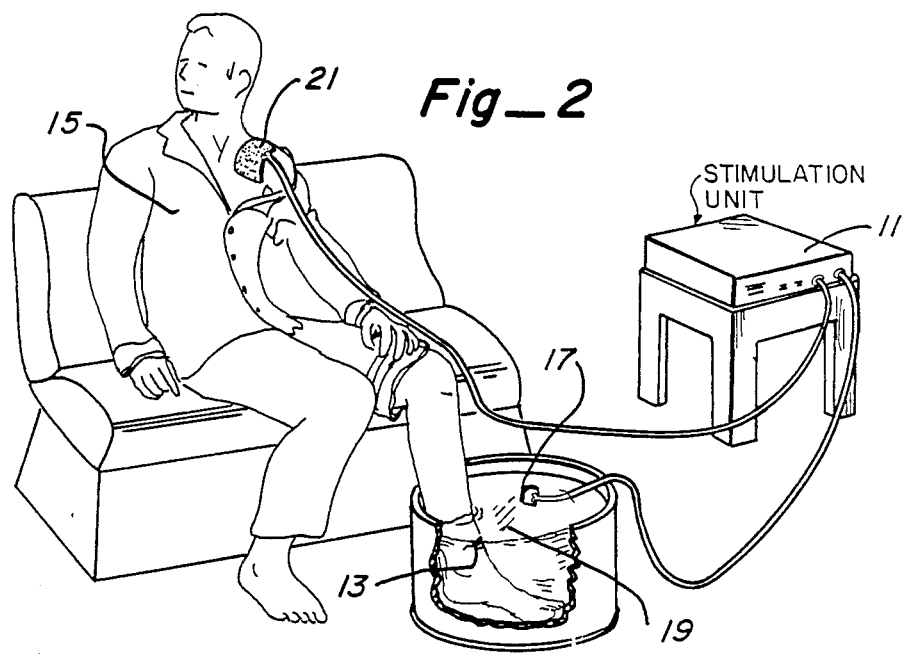
Fig_2

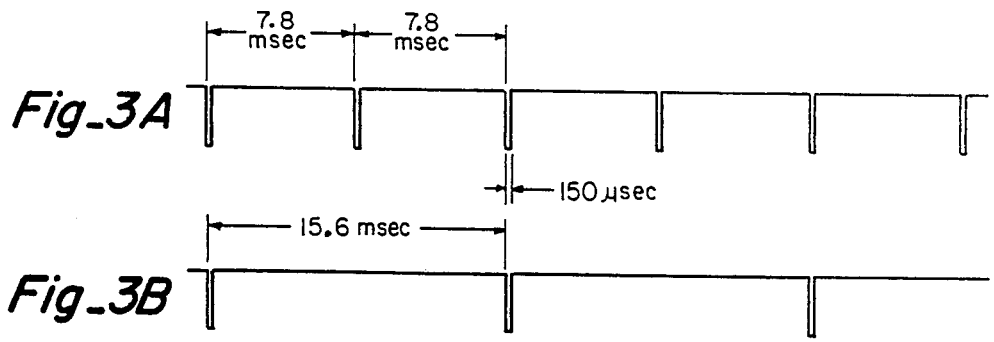
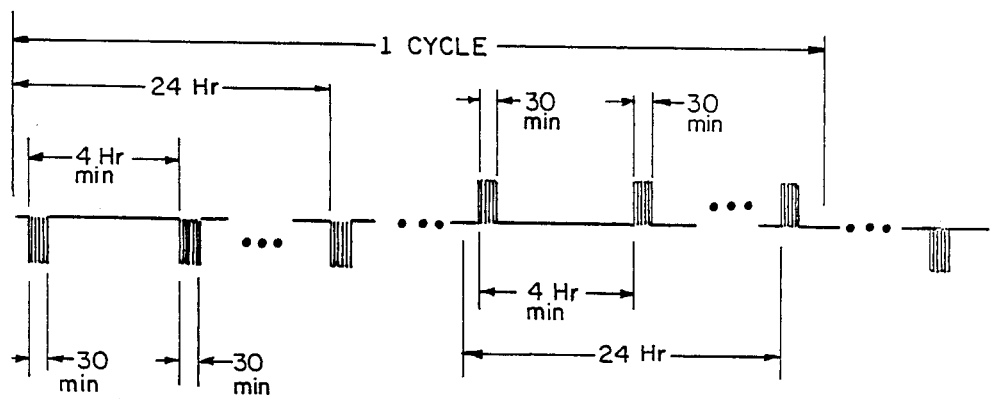
Fig_4
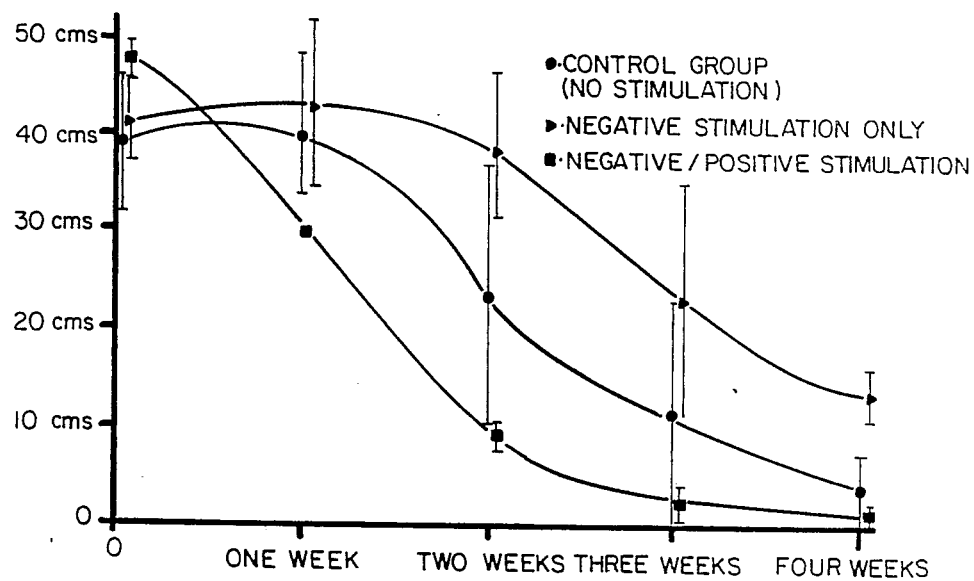
Fig_5

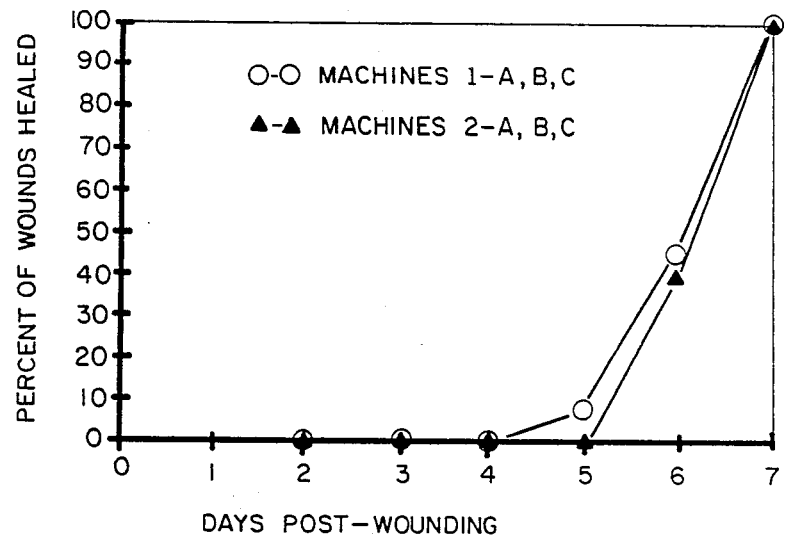
Fig_6A
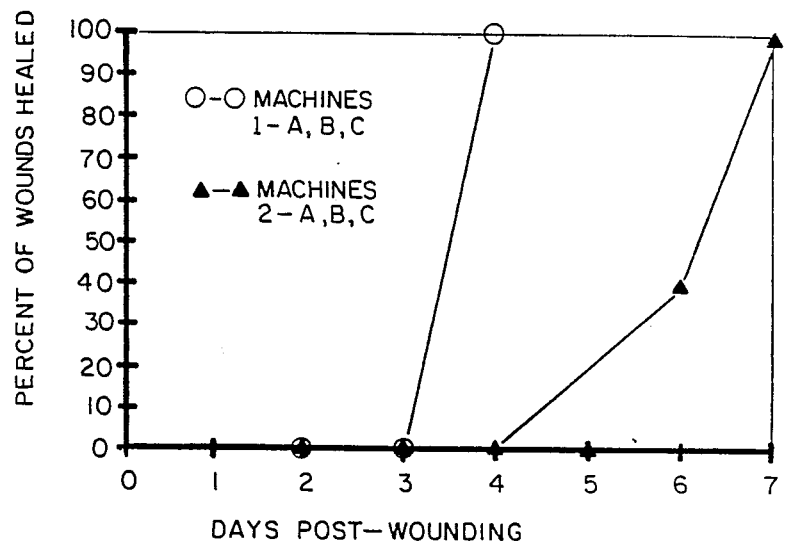
Fig_6B

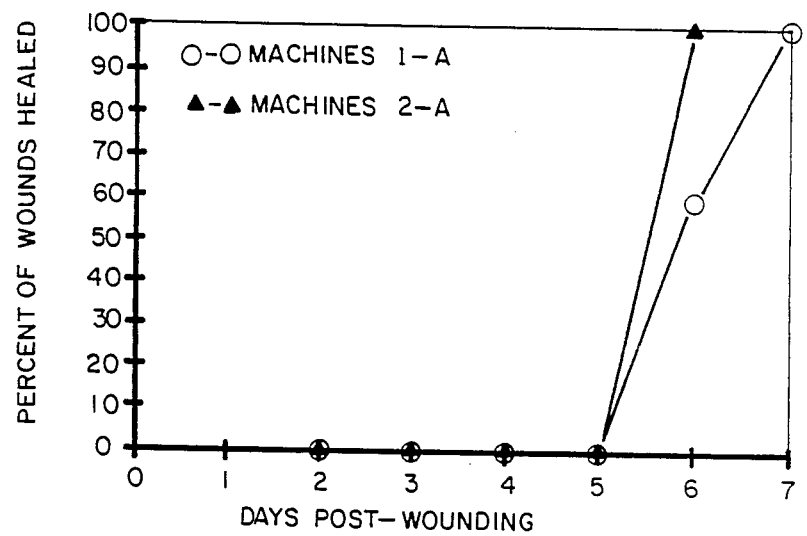
Fig_6C
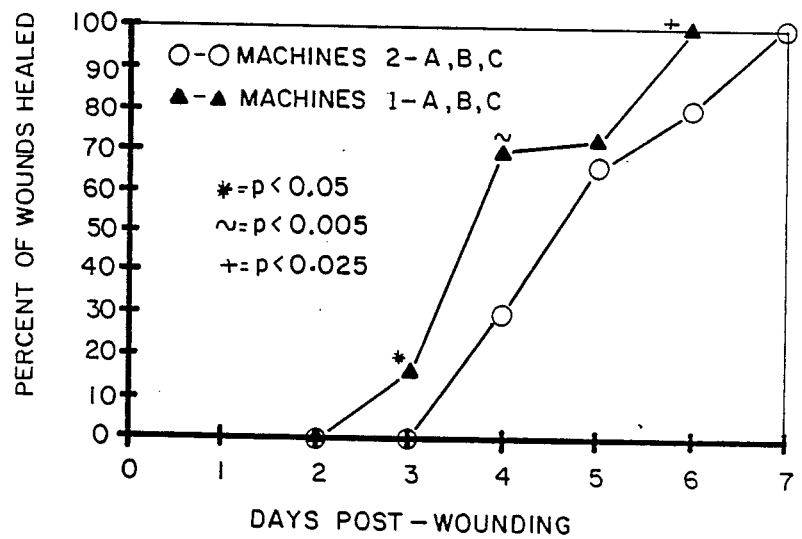
Fig_6D

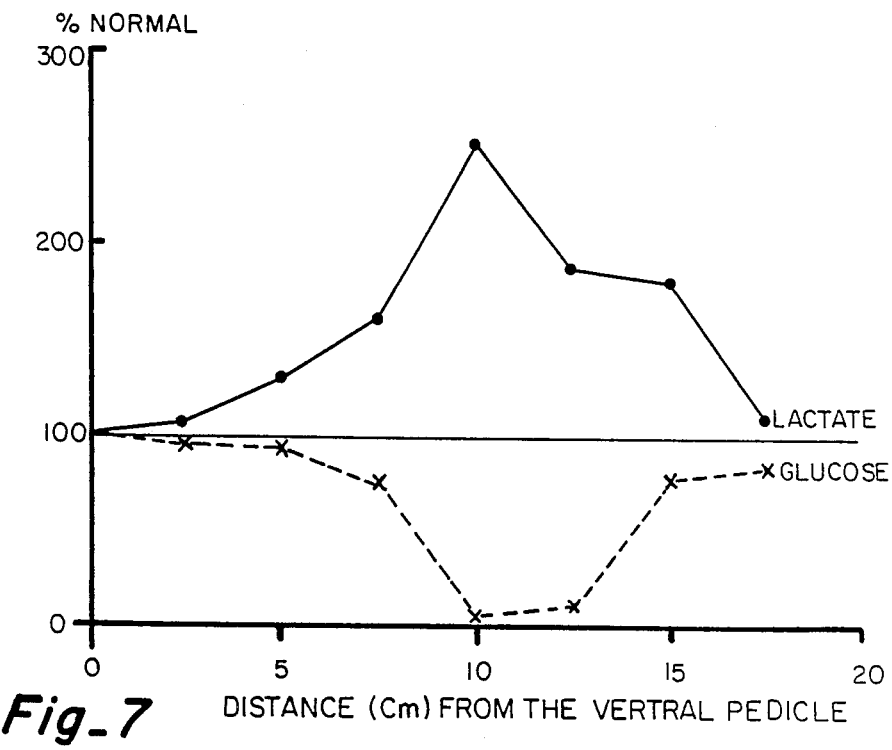
Fig. 7 DISTANCE (Cm) FROM THE VERTRAL PEDICLE
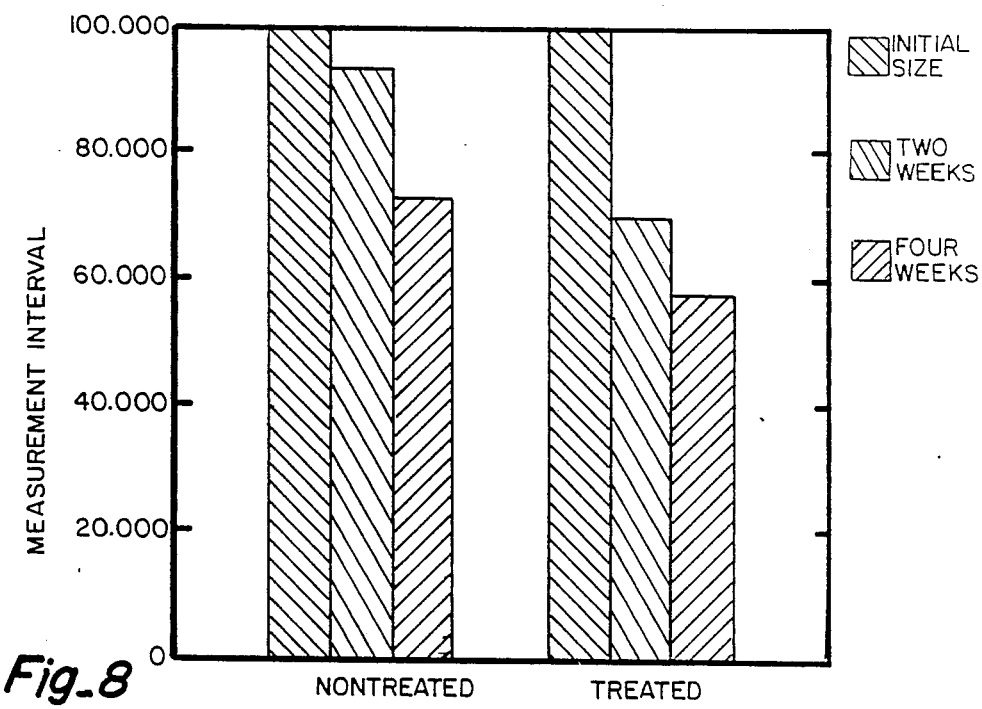
Fig. 8

SOFT TISSUE WOUND HEALING THERAPY UTILIZING PULSED ELECTRICAL STIMULATION

FIELD OF THE INVENTION

This invention relates to wound healing therapy and, more particularly, relates to soft tissue wound healing therapy utilizing pulsed electrical stimulation.

BACKGROUND OF THE INVENTION

Numerous procedures and therapies have been heretofore attempted and/or utilized in connection with treatment of wounds, including application to the wound of various stimulation and/or medicaments to aid the natural body healing functions. It has been found, however, that at least some known stimulations and/or medicaments cannot be utilized for a particular treatment or in connection with particular individuals, and it has also been found that some wounds, including chronic wounds, resist healing even with aggressive and intense treatment.

In particular, it has heretofore been suggested that the healing process might be promoted and/or accelerated through use of electrical stimulation, and several methods for effecting such treatment have been heretofore proposed, with some such methods having been heretofore utilized with varying degrees of success. Among the more successful has been bone growth stimulation for promoting bone healing.

With respect to electrical stimulation to promote healing of soft tissue wounds, or injuries, several procedures have been heretofore suggested, and at least some initial research has indicated that electrical stimulation might be effectively utilized to achieve this end. However, to date, no known method has been suggested that has proved to be completely successful, perhaps due to the many and varied parameters of the many problems presented by such injuries.

A number of articles directed to wound healing have been heretofore published, and several of these articles have suggested various procedures that might be utilized for promoting wound healing. Included in such articles are the following:

Oscar M. Alvarez, Ph.D., Patricia M. Mertz, B. A., Richard V. Smerbeck, B. S., and William H. Eaglstein, M.D., "The Healing of Superficial Skin Wounds Is Stimulated by External Electrical Current", The Journal of Investigative Dermatology, 81:144–148 (1983).

Dennis Assimacopoulos, M.D., "Low Intensity Negative Electric Current in the Treatment of Ulcers of the leg due to Chronic Venous Insufficiency", American Journal of Surgery, 115: 683–687 (1968).

Cyril B. Frank, M.D. and Andrew Y. J. Szeto, Ph.D., "A Review of Electromagnetically Enhanced Soft Tissue Healing", IEEE Engineering In Medicine and Biology Magazine, pages 27–32, December, 1983.

Walter R. Gault, MSPH and Paul F. Gatens, Jr., M.D., "Use of Low Intensity Direct Current in Management of Ischemic Skin Ulcers", Physical Therapy, 56: Number 3, pages 265–269, March, 1976.

Lester E. Wolcott, M.D., Paul C. Wheeler, M.D., Henry M. Harwicke, M.D., and Blair A. Rowley, MEE, "Accelerated Healing of Skin Ulcers by Electrotherapy: Preliminary Clinical Results", Southern Medical Journal, 62: 795–801, July, 1969.

Charles R. Ross, D.P.M. and Donald Segal, D.P.M., "High Voltage Galvanic Stimulation—An Aid To Post-Operative Healing", Current Podiatry, pages 19–25, May, 1981.

Barbara F. Thurman, Maj., USAF, BSC, and Emily L. Christian, Capt., USAF, BSC, "Response of a Serious Circulatory Lesion To Electrical Stimulation", Physical Therapy, Volume 51: Number 10, pages 1107–1110, October, 1971.

Barbara Nickerson, R.P.T., M.S., "High Voltage/Low Intensity Current In Wound Healing", Poster Session APTA National Meeting Phoenix, June 17, 1980.

H. Grady Young, DVM, "Electric Impulse Therapy Aids Wound Healing", Modern Veterinary Practice, December, 1966.

T. K. Akers and A. L. Gabrielson, "The Effect Of High Voltage Galvanic Stimulation On The Rate Of Healing Of Decubitus Ulcers", ISA, pages 99 and 100, 1984.

J. A. Feedar, and L. C. Kloth, "Acceleration Of Wound Healing With High Voltage Pulsating Direct Current", (Abstract), APTA Journal, Volume 65, No. 5, page 741, May 1985.

As brought out in the above-listed articles, it has been suggested: that application of electrical stimulation can promote wound healing; that electrical stimulation can be applied to a wound through electrodes in the presence of saline; that low intensity direct current (LIDC) can be utilized as the applied electrical stimulation; that low intensity direct current (LIDC) can be initially applied as negative current through an active electrode adjacent to the wound; that applied LIDC stimulation can be switched between negative and positive polarities during the course of treatment; that pulses might be applied as the electrical stimulation for achieving wound healing; that high voltage, low amperage galvanic stimulation can be applied to a patient; that high voltage, low amperage galvanic stimulation can be applied to a patient initially through a cathode and later through an anode at the wound; and that high voltage, low amperage galvanic stimulation can be applied for short treatment pulses that are periodically repeated.

In addition, several patents have also been issued directed to promoting healing by electrical stimulation. Included in these patents are the following:

| Patent Number | Inventor | Issue Date |
| --- | --- | --- |
| 2,099,511 | Caesar | November 16, 1937 |
| 3,918,459 | Horn | November 11, 1975 |
| 3,964,477 | Ellis et al | June 22, 1976 |
| 4,019,510 | Ellis | April 26, 1977 |
| 4,233,965 | Fairbanks | November 18, 1980 |
| 4,312,340 | Donadelli | January 26, 1982 |
| 4,313,438 | Greatbatch | February 2, 1982 |
| 4,314,554 | Greatbatch | February 9, 1982 |
| 4,556,051 | Maurer | December 3, 1985 |

The above-listed patents include a showing: that electrical stimulation can be effected at preselected low intensities; that preselected treatment times between a few minutes to a few hours can be utilized; that the polarity of the active electrode can be switched during the course of treatment; and that pulses can be utilized as electrical stimulation.

Thus, as can be appreciated from the foregoing, various procedures, or methods, have been heretofore suggested that utilize many differing parameters. It is felt, however, that procedures, or methods, are still needed that can be demonstrated to enhance healing of soft tissue.

SUMMARY OF THE INVENTION

This invention provides an improved process for enhancing, including promoting and/or accelerating, soft tissue wound healing utilizing pulsed electrical stimulation.

The process of this invention includes application of repeated short treatments of high intensity, substantially rectangular, electrical pulses applied to a soft tissue wound through an active electrode positioned at the wound, and with the dispersive electrode being positioned at a distance from the wound.

The active electrode positioned at the wound is normally caused to provide negative pulses to the wound during a first treatment period of a treatment cycle, and then later is caused to provide positive pulses to the wound during a second treatment period of the treatment cycle, with the treatment cycle being thereafter preferably repeated one or more times in treating most soft tissue wounds. In addition, it has been found that the negative pulses cause debriding of the wound, as well as being useful to reduce edema.

It is therefore an object of this invention to provide an improved process for effecting wound healing.

It is another object of this invention to provide an improved process for enhancing soft tissue wound healing using pulsed electrical stimulation.

It is another object of this invention to provide an improved process for enhancing soft tissue wound healing by applying substantially rectangular pulses of high intensity as electrical stimulation to a wound during repeated short treatment periods.

It is another object of this invention to provide an improved process for enhancing soft tissue wound healing by applying negative pulses to said wound to debride the wound.

It is another object of this invention to provide an improved process for enhancing soft tissue wound healing by first applying substantially rectangular pulses of negative polarity as electrical stimulation to the wound through an active electrode at the wound during a first treatment period, and thereafter applying substantially rectangular pulses of positive polarity as electrical stimulation to the wound through the active electrode during a second treatment period.

It is yet another object of this invention to provide an improved process for soft tissue wound healing wherein negative pulses are applied to the wound during a first treatment period of a treatment cycle, positive pulses are later applied to the wound during a second treatment period of the treatment cycle, and the treatment cycle is thereafter repeated one or more times.

With these and other objects in view, which will become apparent to one skilled in the art as the description proceeds, this invention resides in the novel combination, methods, protocols, and processes substantially as hereinafter described, and more particularly defined by the appended claims, it being understood that changes in the precise embodiments of the herein disclosed invention are meant to be included as come within the scope of the claims.

BRIEF DESCRIPTION OF THE DRAWINGS

The accompanying drawings illustrate use of the invention and results achieved utilizing this invention, as follows:

FIG. 1 is a sketch illustrating, typically, electrode positioning for direct pad application of pulsed electrical stimulation from a stimulation unit;

FIG. 2 is a sketch illustrating, typically, electrode positioning for hydrotherapy application of a pulsed electrical stimulator from a stimulation unit;

FIGS. 3A and 3B are typical waveforms deliverable through the active electrode to a wound;

FIG. 4 is a typical representation of a treatment cycle;

FIGS. 5, 6A, 6B, 6C and 6D are graphs illustrated particular results achieved during pig studies;

FIG. 7 is a graph illustrating glucose and lactate distribution with bipedicle skin flaps on day one post-operatively; and FIG. 8 is a graph illustrating particular results achieved using the now preferred protocols of this invention.

DESCRIPTION OF THE INVENTION

Effective enhancement, including promotion and acceleration, of wound healing is accomplished by this invention utilizing pulsed electrical stimulation.

It has been found, as illustrated in FIGS. 1 and 2, that pulses, delivered from an electrical stimulation unit 11, are preferably applied to a soft tissue wound (indicated generally by the numeral 13) on a body 15 through an active electrode 17 positioned at the wound. Such application can be effected by direct pad application, as indicated in FIG. 1, or can be effected by hydrotherapy, as indicated in FIG. 2, with the pulses being delivered to the wound through active electrode 17 immersed in a saline solution 19.

In either case, a dispersive, or return, electrode 21 is positioned in contact with the body of the patient being treated, with the dispersive electrode being preferably positioned at a distance from the wound, as is indicated in FIGS. 1 and 2. It has been found that at least for some phases of treatment, edema reduction being an example, the dispersive electrode should be as far from the active electrode as possible.

Electrical stimulation unit 11 preferably provides high intensity pulses that are applied through the active electrode to the wound being treated. A unit for providing such pulses is a pulsed galvanic electrical stimulator unit commercially offered for sale by Staodynamics, Inc., the assignee of this invention, and is known as a STAODYN Vara/Pulse Stimulator that has heretofore been shown to be useful for treating conditions such as inflammation, edema, sprain, and muscle spasm (STAODYN is a registered trademark of Staodynamics, Inc.).

The STAODYN Vara/Pulse pulsed galvanic stimulator unit has been utilized in connection with all of the procedures and protocols set forth herein, and such unit is capable of providing substantially constant current rectangular pulses (pulse width × intensity = constant for rectangular pulses) from the active electrode to the wound at rates of 128 pulses per second (pps) with a 150 microsecond ($\mu$sec) pulse width (as indicated in FIG. 3A), 64 pps with a 150 $\mu$sec pulse width (as indicated in FIG. 3B), 32 pps with a 250 $\mu$sec pulse width, 8 pps with a 250 $\mu$sec pulse width, and 2 pps with a 350 $\mu$sec pulse width. The pulse rate of the unit can normally vary about ±2%, while the pulse can normally vary about ±10 μsec.

In addition, the unit can cause delivery of negative or positive pulses from the active electrode with a constant current intensity of between 0 to 100 milliamperes (ma). As used herein, the current intensity of delivered pulses, when referred to in milliamperes, means milliamperes peak. It has also been found that the STAODYN Vara/-Pulse unit normally provides a voltage across a patient of between about 10 to 30 volts peak.

FIG. 4 indicates a typical cycle of soft tissue wound treatment. Multiple pulses of a predetermined polarity (negative pulses as indicated in FIG. 4) are preferably first applied through the active electrode to a soft tissue wound during first short treatment intervals of a first treatment period of a treatment cycle, after which the polarity of the pulses applied through the active electrodes is reversed (to positive pulses as indicated in FIG. 4) during second short treatment intervals of a second treatment period of the treatment cycle.

It has been found that the pulses applied through the active electrode during the first (or initial) intervals of the first treatment period are preferably negative pulses which are repeatedly applied for one or more days, after which positive pulses are applied through the active electrode during the second intervals of the second treatment period to thus complete a treatment cycle that commonly extends for a number of days. The cycle is then normally repeated until healing is completed.

It has also been found that a short treatment period of between about 15 to 45 minutes (with a 30 minute treatment period being now preferred), applying pulses to the active electrode having an intensity of between about 2.8 to 7.0 μcoulombs per pulse (with about 5 μcoulombs per pulse intensity being now preferred) using constant current pulses having an intensity of about 20 to 50 ma (with constant current pulses of about 35 ma being now preferred), at a rate of between about 32 and 128 pulses per second (with rates of 128 pps and 64 pps being now preferred), with the treatment being applied between about 2 to 4 times a day (with a treatment of two times a day being now preferred), and with the applied pulses being alternated between about each 1 to 3 days (depending upon the particular protocol utilized) has been effective in enhancing wound healing and, particularly, in enhancing healing of chronic wounds.

The above parameters of the process were largely empirically developed over a period of about three years during which a variety of procedures and protocols were attempted on a variety of soft tissue wounds utilizing the STAODYN Vara/Pulse pulsed galvanic stimulation unit to provide the necessary pulses delivered through the active electrode.

During the initial stages of development of the process of this invention, a number of parameters were explored using various pulse rates and intensities, various treatment lengths and intervals between treatments, as well as various combinations of pulse polarities and treated wounds.

During this period, about seventy-five or more patients were evaluated and experimentally treated in an attempt to find one or more useful protocols. All of the treated patients had wound histories of long duration (in excess of one year) without achievement of full wound closure using conventional therapies with the wounds including venous stasis ulcers, decubitus ulcers, diabetic neuropathy lesions, open amputee suture lines due to vascular insufficiency, burns, or pemphighoid lesions.

The initial therapy treatment utilized included: application of negative pulses, positive pulses, and alternating negative and positive pulses, at rates between 8 and 128 pps, and at intensities between 20 ma and 100 ma; a treatment time of 2 hours on, 2 hours off continuously, 2 hours on, 2 hours off for 8 hours, and decreasing of treatment time by increments of 15 minutes from 2 hours to 15 minutes until reaching a treatment time of 30 minutes twice daily with not less than 4 hours between treatments (which was initially selected as the best therapeutic treatment time for future development); treatment with pad placement (sponge) directly into the wound, directly over a saline soaked 4×4 gauze, into the wound directly over semi-occlusive dressings, or directly over a saline dressing; treatment with an immersible electrode (used only in a continuous mode at a rate 128 pps with pads negative and positive and at an intensity 30–50 ma); use of a dispersive pad placed on the anterior and posterior body trunk, anterior and posterior thigh, buttocks, abdomen area, the shoulders (high), upper and lower back, sacral area, or calf of leg; and use of a conductor solution including water, lactated ringers, or isotonic saline.

The noted results included: wound hemorrhaging and perimeter deterioration at intensities above 50 ma, with some improvement being noted in the character of the wound, and with no change noted in wounds treated at 20 ma; wounds treated in an interrupted mode showed improvement at intensities above 50 ma, but skin irritation around the wound occurred; and in spite of varied parameters, treated wounds generally showed some improvements either in measurements or character.

More specific applications and results obtained during the initial research are as follows:

TABLE I

| Patient No. | Type Wound | Rate | Intensity | Current Mode |
|---|---|---|---|---|
| 1A | Pilonidal | 128 | 20–40 | Continuous |
| 1B | Cysts | 128 | 20–40 | Continuous |
| 1C | | 64 | 35–45 | Continuous |
| 2 | Decubitus Ulcer | 128 | 50–80 | Continuous |
| 3A | Burns | 128 | 30–50 | Continuous |
| 3B | | 128 | 50–80 | Continuous |
| 4A | Malignant | 128 | 25 | Continuous |
| 4B | Lesions | 128 | 30 | Continuous |
| 4C | | 128 | 25 | Continuous |
| 4D | | 128 | 25–30 | Continuous |
| 5A | Decubitus Ulcer | 128 | 30–60 | Continuous |
| 6A | Sacral | 128 | 35–45 | Continuous |
| 6B | Decubitus | 128 | 30–40 | Continuous |
| 6C | Ulcers | 64 | 30–40 | Continuous |
| 7A | Burn | 14 32 | 30–52 | Continuous |
| 7B | Sacral Decubitus Ulcer | 64 | 40–80 | Continuous |
| 8A | Decubitus Ulcers | 128 | 60 | Interrupted Later Changed to continuous |
| 8B | | 8 | 50 | Continuous |
| 8C | | | 40–50 | |
| 8D | | 32 | 40–60 | Continuous |
| 8E | | 128 | 60 | Continuous |
| 8F | | 64 | 80 | Continuous |
| 8G | | 128 | 30 | Continuous |
| 9A | Abscesses | 128 | 80–100 | Continuous |
| 9B | | | 50–60 | Continuous |
| 9C | | 32 | 50–60 | Continuous |
| 9D | | 32 | 80–100 | Continuous |

TABLE I-continued

| | | | | |
|---|---|---|---|---|
| 9E | | 32 | 80–100 | Continuous |
| 9F | | 128 | 80–100 | Continuous |
| 9G | | 8 | 50–60 | Continuous |
| 9H | | 128 | 80–100 | Continuous |
| 9I | | 8 | 50–60 | Continuous |
| 9J | | 32 | 50–60 | Continuous |
| 9K | | 128 | 50–60 | Continuous |
| 10A | Pemphignoid | 8 | 58 | Interrupted |
| 10B | Lesions | 28 | 80–100 | Continuous |
| 10C | | 8–32 | 40–50 | Continuous |
| 11A | Decubitus | 8–32 | 30–50 | Continuous |
| 11B | Ulcers | 64 | 40–80 | Continuous |
| 12A | Decubitus | 32 | 50–60 | Continuous |
| 12B | Ulcers | 128 | 80–100 | Continuous |
| 13A | Bilateral | 128 | 30–50 | Continuous |
| 13B | Vascular Lesions | 32 | 45 | Continuous |

| Pat. No. | Pad Selection & Placement | Effects |
|---|---|---|
| 1A | Water Immersible Electrode inserted with saline gauze into sinus tract anal.) Neg × 3 days × 30 min | Good red tissue, granulation of tunnel to wound base. |
| 1B | Pos × 3 days × 30 min | |
| 1C | Neg × 3 days × 30 min Pos × 3 days × 30 min Dispersive pad on abdomen | Wound healed in 3 months. |
| 2 | Negative current only. Used 3 devices with electrodes dropped in hubbard tank. Dispersive pads × 3 on shoulders and back, wet dressing between treatments. | Wound debrided and began to granulate so that skin grafts become possible. |
| 3A | Negative-direct pads into wounds. | Contractures made this ineffective - no improvement. Some skin irritation. |
| 3B | Immersible electrodes in hubbard tank. | Evidence of healing without rigid scarring. Took a minimum of 4 months. |
| 4A | Dispersive pad: thigh treatment pads into leg lesions. Negative 30 min. twice a day × 5 days. | |
| 4B | Positive, 30 min, twice a day × 3 days | Could not tolerate direct pad - increased pain during positive. |
| 4C | Dispersive pad - shoulder due to edema decrease in legs. | Tolerated 25 intensity for several days. |
| 4D | Negative only - direct pad. | Then straight negative. Wounds did not heal but edema was reduced and pain decreased. |
| 5A | Dispersive pad: back and thigh. Negative polarity 30 min., twice a day × 7 days or until wound debrided. | Heavy margin then fused eschar covering sacral decubitus. Developed generalized septicemia within 3 days of treatment. Determined that opening must be made into eschar prior to treatment, however eschar became soft - but no opening for drainage. |
| 6A | Neg × 3 days × 45 min twice a day Pos × 3 days × 45 min twice a day Use betadine dressing between treatments. | Severe burn around wound - severe drying of wound bed - deterioration. This happened in 4 days. Treatment held × one week, then changed dressing. |
| 6B | Neg × 3 days × 30 min twice a day | Wound showed improvement, but began to deteriorate at wound edges. |
| 6C | Pos twice a day × 3 days × 30 min Neg twice a day × 3 days × 30 min | Wound healed. |
| 7A | Neg × 3 days (in wound) Dispersive pad - shoulder and back. | Some volume reduction of ulcer noted. Improvements in wound size and character. Severe skin irritation results of E-stim and Betadine noted. Wound hemorrhage caused by negative current forced stop to treatment for 1 week. Errythemia noted peri-wound, very sensitive to touch. Wounds begin to break down around edges. Fungus infection on buttocks at electrode sites. E-stim produced hypertrophic skin in portions of ulcer. Severe skin irritation under all electrodes from stimulation requiring topical meds, treatment ended. |
| 7B | Pos × 3 days (in wound). | |
| 8A | Pos × 3 days (in wound) Dispersive pad | Betadine soaks discontinued prior to E-stim. Area size of ulcer smaller but increase purulent drainage. Hydrogen peroxide irrigation before each E-stim treatment. Continued improvement. |
| 8B | Neg × 3 days (in wound) 4-5 days initially, or until wound is clean. | Developed rash peri-wound. Tried positive current only × 14 days - no improvement - extremely slow healing. |
| 8C | | Purulent draining increased. |
| 8D | Negative | |
| 8E | Pos × 3 days, then alternate with neg. | Good granulation noted. |
| 8F | Began alternating polarities for 3 days, twice a day × 30 min. | Wound progression ceased. Back to neg current, wound cleaned up in 14 days. |
| 8G | Pos twice a day × 30 min Neg Alternate every 3 days | Began flushing wound with normal saline prior to treatment and changing moist dressing once a day. Treatment stopped × 10 days due to wound deterioration and purulent drainage. Treatment discontinued. |
| 9A | Pos × 2 hours twice a day × 3 days | Complaints of pain under all pads. |
| 9B | Neg × 2 hours twice a day × 3 days | Ulcer responding to treatment while in neg current. |
| 9C | Neg × 2 hours twice a day to alternate | P.O. antibiotics ordered for general |

TABLE I-continued

| | | |
|---|---|---|
| | every 3 days with positive current × 2 hours, twice a day for 3 days. Dispersive pad: back. Treatment pads in wound. | infection. Developed monilial infection under dispersive pad and peri-wound. Treatment stopped. |
| 9D | Positive × 15 minutes | Wound worsened. Did not place pads in wound - but on each side, then above wound. |
| 9E | Neg × 7 days × 45 min then pos × 15 min. | |
| 9F | Pos × 30 min twice a day alternate every three days, then alternate. | Elase ointment for debriding. |
| 9G | Same schedule every other day. | No change in wound size. |
| 9H | Pos × 30 min in a.m. | Wound treatment discontinued - didn 'T heal. Skin continued to be irritated. Complaints of pain throughout E-stim treatment. |
| 9I | Neg × 30 min in p.m. | |
| 9J | Neg every other day × 5 days | |
| 9K | Pos every other day × 5 days. | |
| 10A | Alternating pads neg × 2 hours twice a day (4 hours off) × 3 days - then off × 3 days. Dispersive pad placement rotation every day. Treatment pads in wounds. Saline used as conductor. | Some improvement noted in wound character (drainage, no pain). Used duoderm dressing. Treatment continued due to decreased lesion progression. |
| 10B | Pos × 3 days twice a day (2 hours on, 4 hours off) Neg × 3 days twice a day (2 nours on, 4 hours off) Dispersive pad: shoulders. | Treatment discontinued due to wound hemorrhage caused by negative current intensity. Developed abdominal dermatitis region of wounds. Used wet dressings between treatments. Complaints of pain until end of treatment. |
| 11A | Neg twice a day × 30 minutes × 3 days alternate with pos twice a day × 30 minutes × 3 days. | Some improvement noted for 2 weeks. Decubitus worsened - treatment discontinued. |
| 11B | Dispersive pad, rotate shoulders. Treatment pads in wound. Moist dressings on wounds. | |
| 12A | Neg 30 minutes twice a day, alternate every three days. | Evidence of granulation. |
| 12B | Pos: 30 minutes twice a day, alternate every 3 days. | Healed. |
| 13A | Neg × 1 hour twice a day until wounds are debrided of eschar, dispersive pad on abdomen. Water treatment pad in plastic bucket of normal saline (1 tsp per quart). | Took 2 months for wounds to debride - these were large wounds. Skin buds noted in wound and later increased skin bud production noted. |
| 13B | Neg alternating with pos × 30 minutes every day. | Wounds continued to improve and healed. |

Based upon the initial research, a two phase pilot study was undertaken using a pig model in an effort to confirm the initial research.

At the onset of the study, a 60 pound domestic pig was lightly anesthetized and four eight centimeter diameter wounds were made on the animal's side. This wound was made down to the muscular fascia and the tissue removed. Dry sterile dressings were placed on each wound. Starting the following day, electrical stimulation to three of the four wounds was performed for one-half hour, twice a day separated by a four hour interval, with the experiment was continued for three weeks.

A STAODYN Vara/Pulse stimulator unit was used for providing pulsed stimulation with the negative pad on the wounds and with the intensity of applied pulses being at levels felt from past clinical experience to be low, preferred, and high (15 ma, 35 ma, and 50 ma, respectively). A summary of the stimulation settings is set forth in Table II, and resulting wound surface areas are set forth in Table III.

TABLE II (Phase 1)
NEGATIVE PAD ON WOUND

| | | |
|---|---|---|
| #1 Control | | |
| #2 Too Low | 128 pps | |
| | Intensity 15 ma | |
| #3 | 128 pps | |
| | Intensity 35 ma | |
| #4 Too High | 128 pps | |
| | Intensity 50 ma (Just below fasciculations) | |
| ½ hour, 2/day | | |
| Dispersive Electrode at Least 12 inches away from active electrode | | |

1 Left back
2 Left front
3 Right back
4 Right front

TABLE III (Phase One)
WOUND SURFACE AREA
($cms^2$)

| Wound | Zero Time | One Week | Two Weeks | Three Weeks |
|---|---|---|---|---|
| No stim. | 27.29 | 37.65 | 30.21 | 19.00 |
| Low Stim. | | 25.53 | 25.06 | 20.64 |
| Preferred Stim. | 36.66 | 34.01 | 29.81 | 9.20 |
| High Stim | | 29.64 | 28.53 | 15.90 |

Low Stim. is 15 ma at 128 pps
Preferred Stim. is 35 ma at 128 pps
High Stim is 50 ma at 128 pps From my original research, it was felt that a treatment of 128 pps and an intensity of 35 ma would likely prove to be most favorable since at a level of 50 ma, muscle fasciculations begin to occur which can be uncomfortable to a patient, and at a much lower level (i.e., about 15 ma) treatment was not expected to yield as good a result. However, no objective data existed to confirm these preliminary observations, and thus the purpose of this study.

Examination of the Phase One study seemed to confirm the foregoing. Planimetry data showed little effect of stimulation at 15 ma. However, a marked improvement was seen with stimulation at 35 ma, and 50 ma stimulation did not seem to be as beneficial as stimulation as stimulation at 35 ma. The foregoing, however needed to be confirmed in additional animals to thereby establish a dose-response curve to help show the efficacy of electrical stimulation in augmentating the healing of soft tissue wounds.

Since the Phase One study appeared to show a favorable effect on wound healing with negative current stimulation in one animal, Phase Two studies were designed to further evaluate an ideal protocol to be used.

The Phase-Two pilot study was undertaken involving six domestic pigs. At the onset of the study, each 60 pound pig was lightly anesthetized with Ketamine and nitrous oxide. An eight centimeter diameter wound was made on the side of each animal. This wound was made down to muscular fascia and the tissue removed. A light sterile dressing was applied.

Starting the day following surgery, an electrical stimulation protocol was begun (as described hereafter). At weekly intervals the wounds were evaluated by taking a standard photograph for standardized computer assisted planimetry. The protocol was continued for four weeks.

At the conclusion of the study, the wound measurements were evaluated for trends and significance. It was not expected, however, that a statistically solid conclusion could be made from this pilot study because of the many variables being evaluated and the intent to be flexible enough to be able to modify the protocol during the course of the study to maximize the amount of information obtained that would be useful to further studies.

The Phase-Two stimulation settings are set forth in Table IV, and resulting wound surface areas are set forth in Tables V, VI, and VII.

TABLE IV (PHASE II)

| | |
|---|---|
| Pigs 1 and 2: | Negative stimulation to one wound (128 pps, 35 ma) |
| | No Stimulation to second wound (control). |
| Pig 3: | Two control wounds, no stimulation. |
| Pigs 4, 5, 6: | Negative stimulation to one wound (128 pps, 35 ma) for three days followed by positive stimulation (128 pps, 35 ma) for three days. |
| | No stimulation to second wound (control). |

All stimulation was for one-half hour per wound, twice a day, separated by an interval of at least four hours.
Note: For the purposes of the following statistical reporting, the control wound and the 35 ma stimulation wound from phase one is included as it represents identical treatment of identical wounds. This pig is referred henceforth as pig 0.

TABLE V

WOUND AREA (cms$^2$) CONTROLS

| Wks | Dys | Pig 0 | Pig 1 | Pig 2 | Pig 3R | Pig 3L | Pig 5 | Pig 6 |
|---|---|---|---|---|---|---|---|---|
| 0 | 1 | 27.29 | | 30.00 | 42.20 | 44.45 | 47.47 | 47.62 |
| | 2 | | 44.23 | | | | | |
| 1 | 7 | | | | 51.69 | 38.43 | | |
| | 8 | | 37.65 | 45.13 | 32.50 | | | |
| 2 | 14 | | | 38.93 | 39.50 | | 7.93 | 14.58 |
| | 15 | 30.21 | | | 8.26 | 25.24 | | |
| 3 | 20 | | 21.99 | 28.00 | 3.99 | 4.14 | 1.76 | |
| | 21 | 19.00 | | | | | | |
| | 23 | | | | | | | 1.81 |
| | 25 | | | | 2.03 | 2.77 | | |
| 4 | 28 | | 10.58 | | | | | |
| | 31 | | | | 1.55 | 1.87 | 0.76 | 1.21 |
| | 34 | | 5.86 | 6.00 | | | | |
| | 40 | | 5.86 | | | | | |

TABLE VI

WOUND AREA (cms$^2$) STIMULATED WOUNDS

| | | Negative Stim. Only | | | Negative/Positive Stim. | | |
|---|---|---|---|---|---|---|---|
| Wks | Days | Pig 0 | Pig 1 | Pig 2 | Pig 4 | Pig 5 | Pig 6 |
| 0 | 1 | 36.66 | | 45.50 | 49.59 | 46.58 | 53.83 |
| | 2 | | 43.17 | | | | |
| 1 | 7 | | 47.76 | | 30.15 | | |
| | 8 | 34.01 | 43.23 | 52.00 | | | |
| | 10 | | | | 18.85 | | |
| 2 | 14 | | | 42.30 | 44.00 | 7.21 | 9.44 |
| | 15 | 29.81 | | | 6.99 | | |
| 3 | 20 | | 31.96 | 28.00 | 4.3 | | |
| | 21 | 19.20 | | | | | |
| | 23 | | | | | 0.69 | 1.44 |

TABLE VI-continued

WOUND AREA (cms$^2$) STIMULATED WOUNDS

| | | Negative Stim. Only | | | Negative/Positive Stim. | | |
|---|---|---|---|---|---|---|---|
| Wks | Days | Pig 0 | Pig 1 | Pig 2 | Pig 4 | Pig 5 | Pig 6 |
| 4 | 28 | | 15.57 | 11.00 | | | |
| | 31 | | | | | 0.00 | 0.33 |
| | 34 | | 6.70 | 6.00 | | | |
| | 40 | | 6.02 | | | | |

TABLE VII

WOUND AREA (cms$^2$) STATISTICAL SUMMARY

| Time | CONTROL (n = 7) | NEG. STIM. (n = 3) | POS/NEG STIM. (n = 3) |
|---|---|---|---|
| 0 | 40.47 ± 8.33 | 41.78 ± 4.58 | 48.09 ± 2.13 |
| 1 week | 41.08 ± 7.44 (n = 5) | 43.08 ± 9.00 | 30.15(n = 1) |
| 2 weeks | 23.52 ± 13.52 | 38.70 ± 7.75 | 7.88 ± 1.36 |
| 3 weeks | 11.53 ± 11.09 | 23.05 ± 12.16 | 2.14 ± 1.91 |
| 4 weeks | 3.19 ± 4.15 (n = 5) | 13.29 ± 3.23 | 0.17 ± 0.23(n = 3) |

All values are expressed as means ± standard deviation.

FIG. 5 illustrates by graph the results obtained during the Phase II study.

The postulate of the second phase of this animal study was that the electrical stimulation of the open, acute wound could be helpful in the healing of the wound. The protocol was designed to assess wound surface area changes during various types of stimulation (i.e., negative stimulation, and negative stimulation alternating with positive stimulation). Six animals were utilized for this study and a significant amount of information was obtained.

First, it was concluded that the experimental protocol is feasible and is capable of yielding information useful to the overall concept and goals of the project. Second, it appears that there may indeed be an effect on the open wound by the application of external electrical currents. Interestingly, continuous negative stimulation did not seem to offer a significant advantage over no stimulation in the small group of animals studied. However, stimulation with negative and positive current alternating on a three day cycle does seem to be most apparent during the early stages. Further work was still needed, however, to further define the exact parameters that will be the most beneficial.

Further experimental work was therefore later conducted on pigs as follows:

Nine specific pathogen-free (SPF) domestic pigs weighing 15 to 20 kg were conditioned for two weeks prior to initiating the experiment. Seven animals were used in this experiment and two animals served as "conditioned back-ups" should for any reason a substitute animal be necessary. These animals were fed a basal swine diet ad libitum and housed individually in animal facilities meeting AAALAC compliance with controlled temperature (19°–21° C.) and light and dark (12/12 LD).

One the day prior to the start of the experiment, the experimental animal was clipped with standard animal clippers. The skin on the back and both sides of the animal was prepared for wounding by washing with a nonantibiotic soap. On the day of wounding (Day 0), the animal was anesthetized with ketamine 1.7 mg/kg intramuscular and inhalation of halothane, oxygen and nitrous oxide combination.

Using a 3"×3" template, six areas to be wounded were outlined on the paravertebral and thoracic areas of the pig. Twelve to fifteen rectangular wounds 10×7 mm and 0.3 mm deep, were made within each 3"×3" area with a modified electrokeratome fitted with a 7 mm specialized blade. The wounds within the outlined area were separated from one another with at least 15 mm of normal skin.

Six STAODYN Vara/Pulse Stimulator units were used to treat the experimental animals. Three units (1-A,B,C) produced pulsed electrical current and the other three units (2-A,B,C) served as a sham control.

Treatment pads, 3"×3", were saturated with sterile normal saline in sterile petri dishes and secured to each animal's body with velcro straps. At least two inches of non-wounded skin separated each treatment area. A large dispersive pad was saturated with tap water and placed on the ventral thoracic area of the animal. All pads were plugged into an associated STAODYN Vara/Pulse unit.

There was at least a six inch separation between treatment pads and the dispersive pads. The experimental animal was placed in a "pig sling" during the two 30 minute daily treatment. The "pig sling" is a canvas hammock which is attached to a steel frame and has lamb's wool padded openings for the legs of the animal.

In Experiment 1, two animals were wounded according to the methods previously described. One animal received treatment with the active machines (1-A,B,C) and the other animal was treated with the sham machines (2-A,B,C). The treatment pads were placed on the wounded areas in the following treatment outline:
(Day 0 = Day of wounding)
Days 0,2,4,6:
  A-Rate=128 pps
  B-Intensity 35 ma
  C-Continuous stimulation
  D-Pads=Negative
  E-Wounds treated twice daily for 30 minutes
Days 1,3,5,7:
  A-Rate=128 pps
  B-Intensity 35 ma
  C-Continuous stimulation
  D-Pads-Positive
  E-Wounds treated twice daily for 30 minutes For Experiment 1, beginning on Day 2 after wounding (Day 0) and each day thereafter for seven days, all wounds and the surrounding normal skin were excised from one 3"×3" treatment area using a standard width (22 mm) keratome blade set at a depth of 0.5 mm. All specimens that were not excised intact were discarded. The excised skin containing the wound site was incubated in 0.5M sodium bromide at 37° C. for 24 hours, allowing separation of the dermis from the epidermis. After separation, the epidermal sheet was examined macroscopically for defects. Defects were defined as holes in the epidermal sheet or as a lack of epidermal continuum in the area of the wound. The wound was considered healed if there were no defects in the epidermis and not healed if there are one or more defects.

The number of wounds healed (re-epithelized) per day was divided by the total number of wounds sampled and multiplied by 100, as shown in Table VIII.

TABLE VIII

Effect of Pulsed Electrical Stimulation of Epidermal Wound Healing (two animals)

| Treatment | Day 2 | Day 3 | Day 4 | Day 5 | Day 6 | Day 7 |
|---|---|---|---|---|---|---|
| Animal-Pig 7 Active Machines 1-A,B,C | 0/12** (0%) | 0/10** (0%) | 0/10** (0%) | 0/12** (8%) | 5/11** (45%) | 11/11** (100%) |
| Animal-Pig 8 Sham Machines* 2-A,B,C | 0/11** (0%) | 0/12** (0%) | 0/9** (0%) | 0/12** (0%) | 4/10** (40%) | 11/11** (100%) |

*Treatment pads were negative on day 0, 2, 4, 6 and positive on days 1, 3, 4 and 7.
**Data is presented as number of wounds healed per number of wounds assessed.
( ) Percent of wounds healed.

The percentage of wounds healed was then plotted against the days after wounding. A curve was constructed from the data and the time needed for 50% of the wounds to heal was determined, and is shown in FIG. 6A.

The $HT_{50}$ and relative rate of healing were calculated and are found in Table IX.

TABLE IX $HT_{50}$ and Relative Rate of Healing of Wounds Treated with Pulsed Electrical Stimulation

| Treatment | $HT_{50}$# | Relative Rate of Healing |
|---|---|---|
| Animal - Pig 7 Active Machines 1-A,B,C* | 6.1 | +2 |
| Animal - Pig 8 Sham Machines 2-A,B,C | 6.2 | |

The time taken for 50% of the wounds to reepithelize.
*Treatment pads were negative on days 0, 2, 4, 6 and postive on days 1, 3, 5 and 7.
Relative Rate of Healing =
$$\frac{HT_{50} \text{ Control} - HT_{50} \text{ Treatment} \times 100}{HT_{50} \text{ Control}}$$

The animal that was treated with machines 1-A,B,C, initiated re-epithelization one day earlier than the animal which received treatment with the sham machines (2-A,B,C,).

For Experiment 2, one animal was wounded according to the methods previously described and the treatment pads followed the same treatment outline as for Experiment 1 except that the pads remained positive on days 1 through 7 after wounding. Machines 1-A,B,C which were identified as being the active machines were used to treat this animal.

Wounds were evaluated according to the methods described in Experiment 1. The $HT_{50}$ and relative rate of healing were determined and compared to the sham treated animal in Experiment 1. Wounds treated with machines 1-A,B,C, were 100% re-epithelized on day 4 after wounding whereas the sham treated wounds had only initiated re-epithelization on day 6 after wounding. The results are presented in Tables X and XI and in FIG. 6B.

TABLE X

Effect of Pulsed Electrical Stimulation on Epidermal Wound Healing (one animal)

| Treatment | Day 2 | Day 3 | Day 4 | Day 5 |
|---|---|---|---|---|
| Animal - Pig 9 Active Machines* | 0/12** | 0/10** | 6/6** | 8/8** |

TABLE X-continued

Effect of Pulsed Electrical Stimulation on Epidermal Wound Healing (one animal)

| Treatment | Day 2 | Day 3 | Day 4 | Day 5 |
|---|---|---|---|---|
| 1-A,B,C | (0%) | (0%) | (100%) | (100%) |

*Treatment pads were negative on day 0 and positive on days 1-7.
**Data is presented as number of wounds healed per number of wounds evaluated.
( ) Percent of wounds healed.

TABLE XI

HT$_{50}$ and Relative Rate of Healing of Wounds Treated with Pulsed Electrical Stimulation

| Treatment | HT$_{50}$# | Relative Rate of Healing |
|---|---|---|
| Animal - Pig 9 | | |
| Active Machines* | 3.5 | +44% |
| 1-A,B,C | | |
| Sham Machines* | 6.2 | |
| 2-A,B,C | | |

*Treatment pads were negative on day 0 and positive on days 1-7.
Relative Rate of Healing =
$$\frac{HT_{50} \text{ Control} - HT_{50} \text{ Treatment}}{HT_{50} \text{ Control}} \times 100$$
The time taken for 50% of the wounds to reepithelize.

Since a positive effect on epithelization was noted when wounds were treated with negative followed by positive pulsed current, it was decided to examine the use of one STAODYN Vara/Pulse machine and one sham machine on the same animal.

For Experiment 3, four 3"×3" areas to be wounded were outlined and wounded as previously described. One animal was treated with one active machine (1-A) and one sham machine 3 (2-A). The treatment pads followed the same outline as in Experiment 2 with the active machine's treatment pads negative on day 0 (day of wounding) and positive on days one through seven after wounding.

Beginning on Day 2 after wounding (Day 0) and each day thereafter for seven days, five wounds and the surrounding normal skin were excised from one of the treatment areas (active and sham treated). Wounds were evaluated and retained as discussed previously.

The number of wounds re-epithelized per day was divided by the number of wounds sampled and multiplied by 100 as set forth in Table XII.

TABLE XII

Effect of Pulsed Electrical Stimulation on Epidermal Wound Healing (one animal)

| Treatment | Day 2 | Day 3 | Day 4 | Day 5 | Day 6 | Day 7 |
|---|---|---|---|---|---|---|
| Animal-Pig 10 | | | | | | |
| Active Machine 1-A* | 0/5** (0%) | 0/5** (0%) | 0/5** (0%) | 0/5** (0%) | 3/5** (60%) | 3/5** (100%) |
| Sham Machine 2-A* | 0/5 (0%) | 0/5 (0%) | 0/5 (0%) | 0/5 (0%) | 5/5 (100%) | |

*Treatment pads were negative on day 0 and positive on days 1-7.
**Data is presented as number of wounds healed per number of wounds assessed.
( ) Percent of wounds healed.

The percentage of wounds healed was then plotted against days after wounding. A curve was constructed from the data and the time needed for 50% of the wounds to heal was determined as shown in FIG. 6C.

The HT$_{50}$ and relative rate of healing were determined and the active machine treated wounds were compared to sham treated wounds as set forth in Table XIII.

TABLE XIII

HT$_{50}$ and Relative Rate of Healing of Wounds Treated with Pulsed Electrical Stimulation

| Treatment | HT$_{50}$# | Relative Rate of Healing |
|---|---|---|
| Animal - Pig 10 | | |
| Active Machine | 5.8 | −5.4% |
| 1-A | | |
| Sham Machine | 5.5 | — |
| 2-A | | |

The time taken for 50% of the wound to reepithelize.
*Relative Rate of Healing =
HT$_{50}$ Control − HT$_{50}$ Treatment × 100
HT$_{50}$ Control The electrically stimulated wounds had a relative rate of healing −5.4% when compared to sham control on the same animal. The reason that no differences were observed when electrical stimulation was delivered using one active machine and one sham machine to different wounds on the same animal is unknown, but is believed to illustrate a systemic effect. After reviewing our findings, the protocol in Experiment 2 was used to complete more animals for a full study of the effects of electrical stimulation.

For Experiment 4, three additional animals were treated with the active machines (1-A,B,C,) and two other animals were treated with the sham machines (2-A,B,C,). These animals were wounded according to the methods described in Experiment 2 and treatment pads followed the same outline as in Experiment 2 (Day 0; negative pads, Days 1-7; positive pads).

Wounds were evaluated for re-epithelization using the same methods as in Experiment 2.

Treatment with machines 1-A,B,C prevented hard crust formation and produced fasciculation of the skin. Treatment with machines 2-A,B,C allowed semi-hard crust formatin and did not produce fasciculation of the skin.

The data from these animals were combined with the data from the sham animal in Experiment 1 and the treated animal in Experiment 2. The number of wounds healed (re-epithelized) was divided by the total number of wounds sampled and multiplied by 100 as set forth in Table XIV.

TABLE XIV

Effect of Pulsed Electrical Stimulation on Epidermal Wound Healing (combined data: three additional animals plus animal used in Experiment 2 and sham animal from Experiment 1)

| Treatment | Day 2 | Day 3 | Day 4 | Day 5 | Day 6 | Day 7 |
|---|---|---|---|---|---|---|
| Active Machines* 1-A,B,C | 0/48** (0%) | 7/44** (16%) | 27/39** (69%) | 26/36** (74%) | 36/36** (100%) | — |
| Sham Machines* 2-A,B,C | 0/37 (0%) | 0/38 (0%) | 10/33 (30%) | 23/35 (66%) | 24/30 (80%) | 33/33 (100%) |

*Treatment pads were negative on day 0 and positive days 1-7.
**Data is presented as number of wounds healed per number of wounds assessed.
( ) Percent of wounds healed.

The percentage of wounds healed was plotted against days after wounding as shown in FIG. 6D. The HT$_{50}$ or time required for 50% of the wounds to heal was calculated for each treatment using logistics regression analysis and the relative rates of healing were determined for each treatment and is set forth in Table XV.

TABLE XV

HT₅₀ and Relative Rate of Healing of Wounds
Treated with Pulsed Electrical Stimulation

| Treatment | HT₅₀# | Relative Rate of Healing |
|---|---|---|
| Active Machines* 1-A,B,C | 3.8 | +17% |
| Sham Machines* 2-A,B,C | 4.6 | — |

*Treatment pads were negative on day 0 and positive on days 1–7.
The time taken for 50% of the wounds to reepithelize.
Relative Rate of Healing =
$\frac{HT_{50} \text{ Control} - HT_{50} \text{ Treatment}}{HT_{50} \text{ Control}} \times 100$ Statistical evaluation (chi-square using four fold tables) was performed on the data from all treatment groups from each animal (including the data from Experiment 1 and 2). The significance between treatment data is shown in FIG. 9.

Pulsed electrically stimulated wounds treated with negative current on Day 0 (day of wounding) and positive current on Days 1 through 7 after wounding (30 minutes twice daily) re-epithelized significantly faster than sham treated control wounds.

An investigation to determine the effects of pulsed stimulation on the survival rates of skin flaps has also been conducted. In this investigation, Yorkshire pigs, 15 to 20 kg, were sedated with intramuscular ketamine (20 mg/kg), acetylpromazine (1 mg/kg), and atropine (0.2 mg/kg). The animals were intubated with an endotracheal tube and mechanically ventilated. Pentobarbital was given intravenously to maintain a satisfactory level of anesthesia during surgery (20 to 30 mg/kg). Four bipedicle flaps measuring 4×20 cm were created on each animal; 2 flaps on each flank. The skin flaps were created by means of parallel incisions, with undermining in the superficial fascial plane beneath the panniculus carnosus, preserving dorsal and ventral pedicles. The flaps were sutured into position in their donor sites. The ventral pedicles were situated 4 cm from the nipple line, and the dorsal pedicles were situated 3–4 cm from the dosal midline. The flaps were separated from each other by a distance of 6 cm.

The animals were placed in a body sling during electrotherapy. The most ischemic area of the flaps was identified on the basis of tissue glucose and lactate as being 9–13 cm from the ventral pedicle, as shown by FIG. 7. The ischemic areas of the flaps were treated with electrical current using a STAODYN Vara/Pulse stimulation unit. Control animals received either a sham treatment (2 pigs) or no treatment (3 pigs). The experimental group (7 pigs) was treated with negative electrical current for 30 minutes twice daily during the initial 3 days, with positive electrical current during days 4–6, and with negative electrical current during days 7–9. The intensity of the electrical current was 35 milliamperes at a frequency of 128 Hz.

In a separate experiment (3 pigs), two flaps on one side of the animals were treated with electrical current, and the contralateral flaps were used as controls.

Skin biopsies were obtained under anesthesia from the ischemic central portions of the bipedicle flaps on days 3, 6, and 14 following flap elevation. The skin samples were frozen immediately in liquid nitrogen and sectioned (20 um in thickness) vertical to the skin surface in a cryostat ($-25°$ C.). The tissue sections were dried overnight under a vacuum in the frozen state. The lyophilized sections were stored in a vacuum tube at $-20°$ C. until biochemical assays were performed. Full-thickness skin (excluding the panniculus adiposus and panniculus carnosus) were microdissected and weighed (approximately 0.1 mg) on a torsion balance. Tissue glucose, lactate, and ATP (adenosine triphosphate) were measured by enzymatic fluorometric methods. RNA/DNA ratios were determined by fluorometric methods, and malondialdehyde (MDA) levels were determined by the thiobarbutric acid methods.

A total of 48 flaps in 12 animals were observed. The mean proportion of necrosis for each group was expressed as a percentage of total flap area. Table XVI summarizes the results of gross observation.

TABLE XVI

Tissue necrosis in the mid-region of bipedicled skin flaps

| Control | | Electrical Treatment |
|---|---|---|
| Untreated | Sham-treated | |
| 27.1 ± 2.0 (12) | 29.3 ± 3.3 (8) | 13.2 ± 2.3 (28)* |

Tissue necrosis is expressed as a percent of flap area.
Each figure represents a mean ± S.E.M., with the number of flaps in parentheses.
*p < 0.001 vs. either untreated or sham-treated control.

In the control groups, no significant difference was found between the sham-treated and untreated animals. An average of 28% ± 1.7 (mean ± SEM, n-20) of each flap became necrotic within 3 weeks postoperatively. In the experimental group, treatment with electrical current significantly reduced the area of necrosis to an average of 13% (P<0.001): 10 of 28 flaps survived completely, and the remaining 18 flaps exhibited a decrease in the area necrosis to 20% ± 2 (P<0.01).

Histological preparation and histochemical staining for ATPase revealed small blood vessels and the capillary "coils" in the upper layers of the dermis in normal pig skin. The central portion of the flaps exhibited cellular necrosis, and lack of ATPase activities suggested non-functional capillaries in the control flaps on day 3. The flaps treated with electrical current for 3 days also exhibited cellular necrosis in the epidermis. However, the capillaries and perivascular cells appeared to be viable. ATPase activities were moderate in the treated flaps, indicating a restoration of capillary function. The skin flaps exhibited re-epithelization from hair follicles and strong ATPase activities in capillaries following 6 days of treatment. The capillaries of skin flaps were dilated as compared to the normal capillaries.

Table XVII summarizes the results of biochemical arrays of tissue metabolites in the central portions of the bipedicle flaps.

TABLE XVII

Alteration of tissue metabolites in skin flaps following electrical stimulation

| | Post-operative days | | | |
|---|---|---|---|---|
| | 0 | 3 | 6 | 14 |
| Glucose | | | | |
| Control | 10.3 ± 1.26 (5) | 1.08 (2) | 11.8 (2) | 6.8 (2) |
| EC-treated | | 2.80 (2) | 11.2 (2) | 8.1 (2) |
| Lactate | | | | |
| Control | 8.8 ± 0.76 (7) | 20.7 (2) | 14.1 (2) | 11.5 (2) |
| EC-treated | | 18.1 (2) | 16.9 (2) | 13.5 (2) |
| Lactate/Glucose | | | | |
| Control | 0.85 ± 0.05 (5) | 19.1 (2) | 1.19 (2) | 2.34 (2) |
| EC-treated | | 9.9 (2) | 1.51 (2) | 1.67 (2) |
| ATP | | | | |
| Control | 1.57 ± 0.14 (5) | 0.38 (2) | 0.48 (2) | 1.74 (2) |
| EC-treated | | 0.36 (2) | 1.03 (2) | 2.24 (2) |
| Malondialdehyde | | | | |

TABLE XVII-continued

Alteration of tissue metabolites in skin flaps following electrical stimulation

| | Post-operative days | | | |
|---|---|---|---|---|
| | 0 | 3 | 6 | 14 |
| Control | 63.3 ± 7.8 (3) | 226 (2) | 181 (2) | 52 (2) |
| EC-treated | | 150 (2) | 173 (2) | 114 (2) |
| RNA | | | | |
| Control | 2.29 ± 0.77 (6) | 3.16 (2) | 2.57 (2) | — |
| EC-treated | | 3.63 (2) | 2.10 (2) | — |
| DNA | | | | |
| Control | 3.61 ± 0.75 (6) | 5.89 (2) | 4.71 (2) | — |
| EC-treated | | 4.55 (2) | 6.52 (2) | — |
| RNA/DNA ratio | | | | |
| Control | 0.79 ± 0.11 (6) | 0.52 (2) | 0.56 (2) | — |
| EC-treated | | 0.85 (2) | 0.37 (2) | — |

Tissue contents of glucose, lactate, and ATP are expressed as mmoles/kg dry weight, the content of malondialdehyde is umoles/kg dry weight, and the contents of RNA and DNA are g/kg dry weight.
Each figure represents a mean ± S.E.M. with the number of skin flaps in parentheses.

The control flaps exhibited a decrease in glucose and ATP content and an increase in lactate and MDA levels on day 3 postoperatively. The flaps treated with negative electrical current during the initial 3 days demonstated higher glucose and lower lactate levels as compared with the control flaps. The ratio of lactate to glucose was considerably higher in the flaps than in normal skin. The treated flaps demonstrated a lower lactate/glucose ratio than the control flaps. ATP content was 24% of normal in both the control and treated flaps. MDA levels were 3.6 times normal in the control and 2.4 times normal in the treated flaps on day 3. In general, there was no significant difference in the levels of metabolites in the control and treated flaps on days 6 and 14. Tissue glucose returned to normal by day 6. Lactate decreased gradually toward normal following the maximal increase observed on day 3. Lactate/glucose ratios were improved considerably on days 6 and 14. The treated flaps appeared to contain greater ATP content than the control flaps on day 6, but ATP content returned to normal in all flaps by day 14. Flap tissues maintained higher MDA levels during the initial 6 days following operation. No significant alterations of nucleic acid content were found in flap tissues recovering from ischemia.

Treatment with electrical current administered during the initial 9 days following the flap elevation significantly improved flap survival. Improvement of the ratio of lactate to glucose indicates that electrical current enhances capillary circulation. Electrical current appears to stimulate ATP production and prevent lipid peroxidation.

More recently, specific, and now preferred, protocols have been developed for use on soft tissue wounds in an attempt to establish and verify effective use on humans to enhance wound healing. These protocols are as follows:

To effect vascular lesion therapy utilizing a hydrotherapy application: a large dispersive pad is saturated with tap water and placed on a large muscle group a minimum of 12 inches from the treatment area and secured to the patient with velcro belts so that the pad makes good body contact; the extremity to be treated is placed into a small plastic container tall enough to cover all lesion areas and the container is filled with isotonic saline; one or two small silicone immersible electrode pads (if the lesion area is greater than 25 square centimeters (5 cm×5 cm) two silicone immersible pads are used and these pads should be within 10 cm of the lesion area) are placed into the saline in the plastic container immediately adjacent to the lesions (if the lesions are in the mid-leg area, the electrodes may be secured loosely using the velcro pads); the electrodes are then connected to the STAODYN Vara/Pulse unit with the large dispersive pad being connected to the return jack of the unit; and the STAODYN Vara/Pulse controls are set for "Continuous" stimulation, Rate=128 pps, Intensity=35 ma, and Pad selection "negative".

Treatment is effected for 30 minutes twice daily, with a minimum of four hours, and a maximum of 8 hours, between treatments. The parameters set forth are maintained until the wounds exhibit a serosaguineous drainage without a yellow exudate, at which time the intensity is adjusted to 30 ma, after which the pads are made negative×1 day and then made positive×1 day to full wound closure.

For vascular lesion therapy using direct pad application, small treatment pads and a large dispersive pad are utilized. The large dispersive pad is saturated with tap water as described above, and the small treatment pads are saturated with normal saline. A 4×4 gauze dressing which has been wet with normal saline is placed directly over and covering the area to be treated, and the small treatment pads are placed over the gauze dressing, after which all pads are secured to the patient's body with velcro straps. The small treatment pads are then plugged into the STAODYN Vara/Pulse unit, and the large dispersive pad is plugged into the return jack of the STAODYN Vara/Pulse unit. The STAODYN Vara/Pulse controls are set as follows: Rate—128 pps; Intensity=35 ma; "Continuous" stimulation; and Pads "negative".

Treatment is effected for 30 minutes twice daily, with a minimum of four hours, and a maximum of 8 hours, between treatments. The above parameters are maintained until the wound exhibit a serosaguineous drainage without a yellow exudate, after which the intensity is adjusted to 30 ma and the pads are made negative×1 day, and then made positive×1 day to full wound closure.

For decubitus ulcer therapy treatment: flush the wound bed with greater than 30 cc of saline solution before each treatment and keep the wound bed moist with saline solution between treatments; apply clean 4×4 gauze pads moistened with saline solution directly over or into the wound; saturate the large dispersive pad with tap water, place the electrode pads on the wound on top of the gauze pads and secure into place using one or two pads depending on the size and depth of the wound; place the saturated large dispersive pad on a large muscle group a minimum of 12 inches from the treatment area and secure the pad to the patient with velcro belts so that the dispersive pad makes good body contact; place the electrodes into the outlet jacks of the STAODYN Vara/Pulse unit; place the large dispersive pad into the return jack of the STAODYN Vara/Pulse unit, and set the controls of the STAODYN Vara/Pulse unit for "Continuous" stimulation, Rate—128 pps, Intensity—35 ma, and Pad selection "negative".

Treatment is effected for 30 minutes twice daily, with a minimum of four hours, and a maximum of 8 hours, between treatments. The parameters set forth are maintained until the wound has been debrided and is "clean" or a serosaguineous drainage appears, at which time the pads are made negative×3 days, and then made positive×3 days until the wound reaches a Stage II classification, at which time the pulse rate is switched to 64 pps and the pad polarity alternated each day until the wound is completely healed.

For a burn located on the lower extremity, stimulation is used with hydrotherapy application as described below. If the burn is in other locations, the procedures described above for direct pad application are utilized. The STAODYN Vara/Pulse controls are set as follows: "Continuous" stimulation; Rate=128 pps; Intensity=40 ma; and Pad selection "negative".

Treatment is effected for 30 minutes twice daily, with a minimum of four hours, and a maximum of 8 hours, between treatments. When the burn area has healed to the level of the body surface, the rate is reduced to 64 pps and the intensity to 35 ma, and the pad polarity is alternated daily.

The burn area is observed prior to each treatment for evidence of epithelization or skin buds. When this occurs, the treatment pads are maintained positive until full closure of the wound.

For direct pad application to burn area, the STAODYN Vara/Pulse unit controls are set as follows: Rate=128 pps; Intensity=35 ma; "Continuous" stimulation; and Pads "negative" (if the lesion is infected or partially occluded with eschar, however, an intensity of 35 ma is used for a minimum of three days and then switched to an intensity of 30 ma).

Treatment is effected for 30 minutes twice daily, with a minimum of four hours, and a maximum of 8 hours, between treatments. The above settings are maintained until the eschar is removed and the wound is red and beefy in appearance, after which the pad current polarity is switched to a rate of 64 pps and an intensity of 25 ma until full closure of the wound occurs.

For superficial burns with minimal interruption of skin integrity, the same procedures are used as described above for direct pad application, except a rate of 64 pps and intensity of 25 ma are utilized, and pad polarity is made negative for the first treatment and positive for the next treatment with pad polarity being thereafter switched every treatment until the burn area shows evidence of epithelization, after which the pads are made positive for the remaining treatments until healing is complete.

For treatment of graft sites, the pads are prepared in the same way as described above. A sterile 4×4 gauze pad, that is wet with saline, is placed over the graft site, and the treatment pad, saturated with saline, is placed over the 4×4 gauze pad.

The STAODYN Vara/Pulse unit controls are set as follows: Continuous current setting; Rate=128 pps; and Intensity=35 ma. Negative pad polarity is used for three days, after which the pads are switched to positive polarity for 3 days and thereafter alternated in polarity until the site is healed.

For treatment of donor sites, the pads are prepared in the same way as described above. A sterile 4×4 gauze pad, that is wet with saline, is placed over the donor site, and the treatment pad, saturated with saline, is placed over the 4×4 gauze pad. The following Vara/Pulse unit control settings are used: Continuous current setting; Rate=128 pps; and Intensity=35 ma. Pad polarity is made negative for 1 day, then switched to positive polarity until the site is healed.

A number of patients have now been treated utilizing the protocols above set forth. Results obtained are set forth in Table XVIII.

TABLE XVIII

| S/S | St. | PtID | Type | Duration | Actual Size | |
|---|---|---|---|---|---|---|
| Sham | III | 1 | Decub. | 182 | 6.00 | |
| Sham | II | 2 | Decub. | 65 | 4.50 | |
| Sham | III | 3 | Decub. | 8 | 12.25 | (Surgical) |
| Sham | IV | 4 | Decub. | 304 | 5.25 | |
| Sham | IV | 5 | Decub. | 23 | 7.50 | (Vascular) |
| Sham | III | 6 | Decub. | 4 | 12.25 | |
| Sham | III | 7 | Decub. | Unk. | 30.00 | |
| Sham | IV | 8 | Decub. | Unk. | 12.25 | |
| Sham | III | 9 | Decub. | 60 | 6.40 | |
| Sham | II | 10 | Decub. | 2190 | 74.70 | (Surgical) |
| Sham | III | 11 | Decub. | 7 | 67.50 | (Surgical) |
| Sham | IV | 12 | Decub. | 730 | 8.40 | |
| Sham | III | 13 | Decub. | 224 | 5.10 | |
| Sham | III | 14 | Decub. | 365 | 5.55 | |
| Sham | III | 15 | Decub. | 90 | 20.40 | |
| Sham | IV | 16 | Decub. | 90 | 40.00 | |
| Sham | III | 17 | Decub. | 517 | 5.28 | (Vascular) |
| Sham | III | 18 | Decub. | 70 | 4.05 | |
| Sham | III | 19 | Decub. | 182 | 6.76 | |
| Sham | III | 20 | Decub. | 1095 | 41.48 | |
| Sham | IV | 21 | Neuro/Vas | 182 | 15.19 | |
| Sham | III | 22 | Vascular | 486 | 21.50 | |
| Sham | III | 23 | Vascular | 182 | 10.23 | |
| Sham | III | 24 | Vascular | 730 | 40.00 | |
| Sham | III | 25 | Vascular | 2204 | 49.00 | |
| Sham | IV | 26 | Vascular | 173 | 49.00 | |
| Sham | IV | 27 | Vascular | 1226 | 5.88 | |
| Sham | III | 28 | Vascular | 1537 | 26.60 | |
| Sham | IV | 29 | Vascular | 1095 | 28.91 | |
| Sham | IV | 30 | Vascular | 5615 | 7.60 | |
| Sham | III | 31 | Vascular | 730 | 20.35 | |
| Stim. | III | 32 | Decub. | 77 | 5.00 | |
| Stim. | IV | 33 | Decub. | 19 | 15.64 | |
| Stim. | IV | 34 | Decub. | 182 | 21.50 | |
| Stim. | III | 35 | Decub. | 26 | 44.00 | (Surgical) |
| Stim. | III | 36 | Decub. | 8 | 8.64 | (Surgical) |
| Stim. | III | 37 | Decub. | 117 | 6.00 | |
| Stim. | III | 38 | Decub. | 60 | 38.63 | |
| Stim. | III | 39 | Decub. | 27 | 7.00 | (Trauma) |
| Stim. | III | 40 | Decub. | 2 | 5.85 | (Other) |
| Stim. | III | 41 | Decub. | 6 | 9.89 | (Surgical) |
| Stim. | III | 42 | Decub. | 6 | 4.00 | |
| Stim. | III | 43 | Decub. | 79 | 4.60 | (Surgical) |
| Stim. | III | 44 | Decub. | Unk. | 12.50 | |
| Stim. | III | 45 | Decub. | 175 | 4.80 | |
| Stim. | III | 46 | Decub. | 14 | 40.50 | |
| Stim. | IV | 47 | Decub. | 241 | 9.28 | (Vascular) |
| Stim. | III | 48 | Decub. | 72 | 16.25 | (Surgical) |
| Stim. | III | 49 | Decub. | 90 | 4.95 | |
| Stim. | III | 50 | Decub. | 30 | 8.00 | |
| Stim. | III | 51 | Decub. | 231 | 9.00 | |
| Stim. | III | 52 | Decub. | Unk. | 22.80 | |
| Stim. | III | 53 | Decub. | 189 | 21.00 | |
| Stim. | III | 54 | Decub. | 7 | 17.39 | (Surgical) |
| Stim. | III | 55 | Burn | 259 | 9.02 | |
| Stim. | IV | 56 | Neuro | 42 | 4.92 | |
| Stim. | III | 57 | Neuro. | 60 | 5.25 | |
| Stim. | IV | 58 | Vascular | 31 | 16.56 | |
| Stim. | III | 59 | Vascular | 730 | 59.20 | |
| Stim. | III | 60 | Vascular | 409 | 40.32 | (Surgical) |
| Stim. | IV | 61 | Vascular | 365 | 42.12 | |
| Stim. | IV | 62 | Vascular | 4745 | 8.55 | |
| Stim. | III | 63 | Vascular | 140 | 33.21 | |
| Stim. | III | 64 | Vascular | 1460 | 4.00 | |
| Stim. | III | 65 | Vascular | 28 | 5.10 | |
| Stim. | III | 66 | Vascular | 182 | 12.50 | |
| Stim. | III | 67 | Vascular | 587 | 20.90 | |
| Sham | III | 68 | Decub. | 34 | 12.00 | delete |
| Sham | II | 69 | Decub. | Unk. | 11.60 | delete |
| Sham | II | 70 | Decub. | Unk. | 3.84 | delete |
| Sham | III | 71 | Decub. | Unk. | 3.60 | delete |
| Sham | IV | 72 | Vascular | 2555 | 0.48 | delete |
| Sham | IV | 73 | Vascular | 2555 | 0.96 | delete |
| Sham | IV | 74 | Vascular | 2555 | 0.06 | delete |
| Sham | III | 75 | Vascular | 7300 | 2.45 | delete |
| Sham | III | 76 | Vascular | 1623 | 3.10 | delete |

TABLE XVIII-continued

| | | | | | | |
|---|---|---|---|---|---|---|
| Sham | III | 77 | Vascular | 7300 | 1.36 | delete |
| Sham | IV | 78 | Vascular | 2555 | 1.80 | delete |
| Sham | II | 79 | Vascular | 730 | 285.60 | delete |
| Stim. | III | 80 | Decub. | 44 | 5.50 | delete |
| Stim. | III | 81 | Decub. | 1128 | 30.15 | delete |
| Stim. | IV | 82 | Decub. | 304 | 9.38 | delete |
| Stim. | III | 83 | Decub. | Unk. | 2.10 | delete |
| Stim. | III | 84 | Decub. | 51 | 41.25 | delete |
| Stim. | IV | 85 | Decub. | Unk. | 17.10 | delete |
| Stim. | III | 86 | Decub. | 200 | 5.40 | delete |
| Stim. | IV | 87 | Decub. | 72 | 20.25 | delete |
| Stim. | III | 88 | Decub. | 168 | 1.32 | (Surgicdelete) |
| Stim. | III | 89 | Decub. | 118 | 3.84 | delete |
| Stim. | III | 90 | Vascular | 5475 | 8.16 | (Vasculdelete) |
| Stim. | III | 91 | Vascular | 193 | 96.00 | delete |
| Stim. | III | 92 | Vascular | 2232 | 46.25 | delete |
| Stim. | IV | 93 | Vascular | 201 | 45.50 | delete |
| Stim. | III | 94 | Vascular | 486 | 23.32 | delete |
| Stim. | II | 95 | Vascular | 1825 | 77.00 | delete |
| Stim. | IV | 96 | Vascular | 319 | 19.76 | delete |
| Stim. | III | 97 | Vascular | 1460 | 162.00 | delete |

| PtID | Week 2 | Week 4 | Week 6 | Week 8 |
|---|---|---|---|---|
| 1 | 62.50 | 90.00 | | |
| 2 | 11.11 | 7.78 | | |
| 3 | 45.71 | 5.31 | | |
| 4 | 178.57 | 178.57 | | |
| 5 | 66.67 | 21.33 | 8.00 | |
| 6 | 17.96 | 83.59 | | |
| 7 | 40.83 | 108.33 | | |
| 8 | 222.69 | 139.59 | | |
| 9 | 26.56 | 0.00 | | |
| 10 | 96.72 | 81.39 | | |
| 11 | 57.04 | 6.40 | | |
| 12 | 72.38 | 31.25 | | |
| 13 | 117.65 | 37.65 | | |
| 14 | 97.29 | 100.90 | | |
| 15 | 80.88 | 66.18 | | |
| 16 | 60.00 | 28.12 | | |
| 17 | 79.55 | 51.52 | | |
| 18 | 72.59 | 65.68 | | |
| 19 | 107.84 | 142.01 | | |
| 20 | 85.34 | 90.89 | | |
| 21 | 128.40 | 133.33 | | |
| 22 | 100.00 | 100.00 | | |
| 23 | 69.89 | 51.32 | | |
| 24 | 82.50 | 64.60 | | |
| 25 | 19.31 | 97.04 | | |
| 26 | 105.80 | 92.86 | | |
| 27 | 63.78 | 37.41 | | |
| 28 | 77.59 | 58.80 | 44.25 | |
| 29 | 94.29 | 89.66 | | |
| 30 | 133.42 | 102.24 | | |
| 31 | 408.16 | 184.77 | | |
| 32 | 75.00 | 72.00 | 85.00 | 42.00 |
| 33 | 35.17 | 10.55 | 1.60 | |
| 34 | 88.88 | 92.09 | 87.91 | 78.14 |
| 35 | 75.00 | 39.45 | 19.09 | 5.09 |
| 36 | 81.48 | 6.94 | | |
| 37 | 30.00 | 4.17 | 0.00 | |
| 38 | 23.30 | 1.29 | 0.21 | 0.08 |
| 39 | 91.07 | 75.00 | 60.00 | 42.86 |
| 40 | 85.47 | 68.38 | | |
| 41 | 54.60 | 0.40 | | |
| 42 | 28.00 | 21.00 | 3.00 | |
| 43 | 33.91 | 48.04 | | |
| 44 | 112.00 | 70.56 | 43.20 | 13.20 |
| 45 | 54.17 | 15.63 | 31.25 | 12.50 |
| 46 | 90.25 | 66.44 | 35.85 | 25.93 |
| 47 | 96.98 | 90.95 | | |
| 48 | 40.62 | 4.62 | 0.37 | |
| 49 | 24.24 | 34.14 | | |
| 50 | 80.00 | 75.00 | 57.50 | 50.00 |
| 51 | 35.56 | 18.33 | | |
| 52 | 105.61 | 62.72 | | |
| 53 | 77.38 | 49.71 | 44.52 | 38.67 |
| 54 | 60.72 | 19.84 | | |
| 55 | 81.49 | 33.15 | | |
| 56 | 31.71 | 173.98 | | |
| 57 | 92.57 | 112.76 | | |
| 58 | 95.95 | 65.40 | 34.78 | 16.67 |
| 59 | 70.95 | 175.91 | | |
| 60 | 72.92 | 46.88 | 21.60 | 14.43 |
| 61 | 76.92 | 73.72 | | |
| 62 | 95.91 | 81.52 | 72.98 | |
| 63 | 104.88 | 105.96 | | |
| 64 | 9.00 | 30.00 | | |
| 65 | 105.88 | 90.00 | | |
| 66 | 96.00 | 51.52 | 32.40 | 37.60 |
| 67 | 88.76 | 80.96 | 80.96 | |
| 68 | 350.00 | 0.00 | 0.00 | 0.00 |
| 69 | 112.07 | 0.00 | 0.00 | 0.00 |
| 70 | 106.25 | 0.00 | 0.00 | 0.00 |
| 71 | 119.44 | 58.33 | | |
| 72 | 160.42 | 75.00 | 0.00 | 0.00 |
| 73 | 100.00 | 57.29 | 0.00 | |
| 74 | 200.00 | 0.00 | 0.00 | 0.00 |
| 75 | 100.00 | 204.08 | 269.39 | |
| 76 | 435.48 | 100.65 | | |
| 77 | 100.00 | 112.50 | 88.24 | |
| 78 | 102.78 | 50.56 | | |
| 79 | 105.28 | 83.49 | | |
| 80 | 101.82 | 0.00 | 0.00 | |
| 81 | 114.63 | 91.94 | 134.66 | 127.20 |
| 82 | 53.33 | 32.00 | | |
| 83 | 90.00 | 95.24 | | |
| 84 | 26.67 | 15.44 | 12.73 | 4.41 |
| 85 | 110.29 | | 78.60 | |
| 86 | 64.81 | 66.67 | 16.30 | 38.70 |
| 87 | 149.38 | | | |
| 88 | 96.97 | 98.48 | 71.59 | |
| 89 | 125.00 | 287.50 | | |
| 90 | 54.41 | | | |
| 91 | 86.94 | 0.00 | 0.00 | 0.00 |
| 92 | 121.10 | 133.81 | 173.79 | 204.04 |
| 93 | 100.00 | 140.66 | | |
| 94 | 100.00 | 92.20 | 81.82 | |
| 95 | 89.62 | 0.00 | 0.00 | 0.00 |
| 96 | 92.31 | 0.00 | 0.00 | 0.00 |
| 97 | 91.39 | 89.63 | 98.67 | |

With respect to the results set forth in Table XVIII, the first 67 entries have acceptable data (the remaining 30 entries have data that could not be analyzed for a variety of reasons). Analysis of data for the first listed 67 entries is set forth in Table XIX (by categories of wounds treated), and Table XX (all wounds analyzed).

TABLE XIX

| Group Statistics | Size Mean | S.D. | 4-Week# Mean | S.D. | N |
|---|---|---|---|---|---|
| Sham Decub. | 18.78 | 20.70 | 66.82 | 49.62 | 20 |
| Stim. Decub. | 14.66 | 11.70 | 41.18 | 30.43 | 23 |
| Sham Vascular | 25.91 | 15.19 | 87.87 | 38.89 | 10 |
| Stim. Vascular | 26.25 | 17.64 | 80.19 | 38.26 | 10 |
| Sham "Other" | 15.19 | 0.00 | 133.33 | .00 | 1 |
| Stim. "Other" | 6.40 | 1.86 | 106.63 | 57.66 | 3 |

*Normalized Percent

TABLE XX

| Group Statistics | Size Mean | S.D. | 4-Week# Mean | S.D. | N |
|---|---|---|---|---|---|
| All Sham | 20.96 | 19.05 | 75.76 | 47.77 | 31 |
| All Stim. | 16.63 | 14.19 | 57.47 | 42.30 | 36 |

*Normalized Percent

As shown by Table II and the graph of FIG. 8, sham patients had about 27% of their wounds healed at the end of four weeks, while stimulated patients has about 43% of their wounds healed at the end of four weeks of treatment.

While the mechanism for achieving the results above set forth is not fully understood, it is believed that the application of pulses of electrical stimulation, particularly with utilization of alternating negative and positive rectangular pulses and/or with short treatment times, as specified and set forth herein, results in an improved method for enhancing soft tissue wound healing.

Different physiological effects are produced by application of negative and positive electrodes. With respect to positive current, the following physiological effects have been observed—vaso constricts, dehydrates tissue, decreases pain of acute nature, and germicidal effect. With respect to negative current, the following physiological effects have been observed—vasodilation, decreases pain of chronic nature, products hyperemia, germicidal effect, and more efficient stimulation of nerves.

Since it has been found that wound healing in a deep wound cannot begin until edema is reduced, this can be first accomplished by application of negative pulses directly to the wound. In addition, since it has been found that wound healing cannot begin until the wound has been debrided and cleansed, this can also be first accomplished by applying negative pulses. Thus, by first applying negative pulses to the wound, edema is reduced and the wound debrided and cleansed (negative pulses also stimulate the growth of granulation tissue in at least some wound stages), prior to application of positive pulses which stimulate the growth of epidermis.

Alternation of polarity each predetermined period (such as each day or period of days) can produce continued healing of a deep wound, while continuous use of one polarity of pulses might not sustain wound healing (and might even eventually make the wound larger). As the wound heals and shrinks, by maintaining the electrode and settings constant, the current density over the wound is constant and the nerve stimulation potential remains constant. This means that toward completion of healing, newly healed tissue at the margin of the wound is treated along with the wound.

Negative current also tends to liquify crust and thereby strip off blood clots and cause bleeding, while positive current can be used to control bleeding after a surgical debridement. Both are important in wound healing.

To promote wound healing by pulsed stimulation according to this invention, it is believed that it can be interpreted as artificially increasing the inflammation process. When tissue is injured, the body responds with a standard inflammation process that brings blood, nutrients, hormones, platelets, and white blood cells to the wound site to begin the repair process. Without inflammation, there can be no healing. If a wound does not heal in a normal manner, because of decreased circulation or other causes, the natural inflammation process of the body is not active and a chronic wound can become established. It is believed that the process of this invention helps to heal a chronic wound by reestablishing the inflammation process (after the original cause of the wound has been removed).

As can be appreciated from the foregoing, it is felt that it has been shown that wound healing can be enhanced by pulsed electrical stimulation, and that such enhancement is shown by the test results set forth herein confirming the effectiveness of the methods of this invention as set forth herein.

Accordingly, it is felt that this invention enhances wound healing using pulsed electrical stimulation with the best mode so far devised for the practical application of the principles thereof being set forth herein.

What is claimed is:

1. A method for enhancing soft tissue wound healing utilizing pulsed electrical stimulation, said method comprising:
   positioning an active electrode at a wound to be treated;
   positioning a dispersive electrode at a body having said wound thereon with said dispersive electrode engaging said body at a position spaced from said wound to be treated;
   applying substantially rectangular pulses of electrical energy of predetermined polarity and having a high intensity of at least about 2.8 microcoulombs per pulse through said active electrode to said wound during repeated intervals of a first treatment period with said intervals being of timewise short duration relative to the time elapsed between application of said pulses; and
   applying substantially rectangular pulses of electrical energy of a polarity opposite to that of said predetermined polarity and having a high intensity of at least about 2.8 microcoulombs per pulse through said active electrode to said wound during repeated intervals of a second treatment period that follows said first treatment period.

2. The method of claim 1 wherein said high intensity substantially rectangular pulses have a pulse width of at least about 140 microseconds.

3. The method of claim 1 wherein said applied pulses are substantially constant current pulses having an intensity of at least about 20 milliamperes.

4. The method of claim 3 wherein said applied pulses have an intensity of between about 20 milliamperes and 50 milliamperes.

5. The method of claim 4 wherein said applied pulses have an intensity of about 35 milliamperes.

6. The method of claim 1 wherein said pulses are applied at an intensity of between about 2.8 and 7.0 microcoulombs per pulse.

7. The process of claim 6 wherein said pulses are applied at an intensity of about 5 microcoulombs per pulse.

8. The method of claim 1 wherein said pulses are applied at a rate of between about 32 pulses per second and 128 pulses per second.

9. The method of claim 1 wherein said pulses are applied at a rate of about 128 pulses per second.

10. The method of claim 1 wherein said pulses are applied for repeated intervals of between about 15 and 45 minutes.

11. The method of claim 1 wherein said pulses are applied for repeated intervals of about 30 minutes.

12. The method of claim 1 wherein said pulses are applied for repeated intervals having an elapsed time therebetween of at least about 4 hours.

13. The method of claim 1 wherein said method is utilized for treatment of one of partial thickness and full thickness open skin wounds.

14. The method of claim 13 wherein said method is sued for one of chronic ulcers, burns, and skin flaps.

15. The method of claim 1 wherein said active electrode is smaller in size than is said dispersive electrode.

16. The method of claim 1 wherein said predetermined polarity of said applied
   high intensity pulses of electrical energy have a negative polarity to cause debriding of said wound.

17. The method of claim 16 wherein said applied high intensity pulses of negative polarity also cause reduction of edema while said wound is being debrided.

18. A method for enhancing soft tissue wound healing utilizing pulsed electrical stimulation, said method comprising:
   positioning an active electrode at a wound to be treated so that said active electrode is contiguous to said wound to be treated;
   positioning a dispersive electrode at the body having said wound thereon with said dispersive electrode being spaced from said wound to treated so that said dispersive electrode engages said body at a position spaced from said wound to be treated;
   applying substantially rectangular pulses of electrical energy of negative polarity and having a high intensity of at least 2.8 microcoulombs per pulse through said active electrode to said wound during repeated intervals with said intervals being of timewise short duration relative to the elapsed time between application of said pulses; and
   applying substantially rectangular pulses of electrical energy of positive polarity and having a high intensity of at least 2.8 microcoulombs per pulse through said active electrode to said wound during repeated intervals with said intervals being of timewise short duration relative to the elapsed time between application of said pulses, and with said positive polarity pulses being applied after said negative polarity pulses have been applied for a preselected time period.

19. The method of claim 18 wherein said negative and positive pulses are applied for substantially equal time intervals, and wherein said elapsed times between application of said negative and positive pulses are substantially equal.

20. The method of claim 18 wherein said step of applying negative pulses and said step of applying positive pulses form a treatment cycle, and wherein said treatment cycle is repeated at least once.

21. The method of claim 18 wherein said applied negative and applied positive pulses are caused to be applied at a rate of between about 32 and 128 pulses per second at an intensity of between about 2.8 and 7 microcoulombs per pulse and are applied for between about 15 and 45 minutes during each treatment interval, with said treatment intervals being caused to occur between about two and four times during a treatment period.

22. The method of claim 21 wherein said applied negative and positive pulses are applied as constant current pulses having an intensity of between about 20 and 50 milliamperes.

23. The method of claim 18 wherein said applied negative and positive pulses are caused to be applied at a rate of about 128 pulses per second and at an intensity of about 5 microcoulombs per pulse for an interval of about 30 minutes twice a day with about a four hour period between applied pulse intervals.

24. The method of claim 23 wherein said applied negative and positive pulses are applied as constant current pulses having an intensity of about 35 milliamperes.

25. The method of claim 18 wherein each of said negative and positive pulses cause a voltage through said body between said active electrode and said dispersive electrode of between about 10 to 30 volts peak.

26. The method of claim 18 wherein said repeated intervals of application of said negative pulses causes debriding of said wound.

27. The method of claim 26 wherein said cycle of treatment is repeated until wound healing is substantially completed.

28. A method for enhancing soft tissue wound healing utilizing pulsed electrical stimulation, said method comprising:
   applying negative pulses to a soft tissue wound at a rate of between about 32 and 128 pulses per second at high intensity intensity of between about 2.8 and 7.0 microcoulombs per pulse for an interval of between 15 and 45 minutes with the negative pulses being applied about twice to four times a day for a predetermined period of time;
   later applying positive pulses to said soft tissue wound at a rate and intensity and for a time interval and period of time substantially the same as that of said negative pulse applications, with said application of said negative pulses followed by said application of said positive pulses being a cycle of treatment; and
   repeating said cycle of treatment at least once.

29. The method of claim 28 wherein said negative and positive pulses are applied as constant current pulses having an intensity of between about 20 and 50 milliamperes.

30. The method of claim 29 wherein said constant current pulses have an intensity of about 35 milliamperes.

31. The method of claim 28 wherein said negative and positive pulses are applied at a rate of about one of 64 and 128 pulses per second at an intensity of about 5 microcoulombs per pulse for an interval of about 30 minutes twice a day.

* * * * *